US011684697B2

(12) United States Patent
Hoerstrup et al.

(10) Patent No.: US 11,684,697 B2
(45) Date of Patent: Jun. 27, 2023

(54) TISSUE-ENGINEERED MEDICAL DEVICE

(71) Applicant: UNIVERSITÄT ZÜRICH, Zurich (CH)

(72) Inventors: Simon-Philipp Hoerstrup, Zurich (CH); Maximilian Y. Emmert, Zurich (CH); Frank Baaijens, Eindhoven (NL); Anita Driessen-Mol, Rosmalen (NL)

(73) Assignee: UNIVERSITÄT ZÜRICH, Zurich (CH)

( * ) Notice: Subject to any disclaimer, the term of this patent is extended or adjusted under 35 U.S.C. 154(b) by 388 days.

(21) Appl. No.: 16/644,066

(22) PCT Filed: Aug. 28, 2018

(86) PCT No.: PCT/EP2018/073076
§ 371 (c)(1),
(2) Date: Mar. 3, 2020

(87) PCT Pub. No.: WO2019/042961
PCT Pub. Date: Mar. 7, 2019

(65) Prior Publication Data
US 2021/0060208 A1 Mar. 4, 2021

(30) Foreign Application Priority Data
Sep. 4, 2017 (EP) .................................. 17189221

(51) Int. Cl.
*A61L 27/36* (2006.01)
*C12N 5/071* (2010.01)
(Continued)

(52) U.S. Cl.
CPC ........ *A61L 27/3616* (2013.01); *A61F 2/2415* (2013.01); *A61L 2/206* (2013.01);
(Continued)

(58) Field of Classification Search
CPC ............... A61F 2/2415; A61L 2430/20; A61L 2430/40; A61L 2420/02; C12N 5/069–0697
See application file for complete search history.

(56) References Cited

U.S. PATENT DOCUMENTS

2016/0220361 A1* 8/2016 Weber ..................... A61L 27/18

FOREIGN PATENT DOCUMENTS

EP 2 853 237 A1 4/2015

OTHER PUBLICATIONS

Petra E. Dijkman et al., "Decellularized homologous tissue-engineered heart valves as off-the-shelf alternatives to xeno- and homografts", Biomaterials, Mar. 4, 2012, pp. 4545-4554, vol. 33, No. 8, XP028411029.

(Continued)

*Primary Examiner* — Thaddeus B Cox
(74) *Attorney, Agent, or Firm* — Sughrue Mion, PLLC

(57) ABSTRACT

The present invention concerns a tissue-engineered medical device, as well as a method for the production said medical device, comprising the following steps: providing a polymer scaffold comprising a mesh comprising polyglycolic acid, and a coating comprising poly-4-hydroxybutyrate; application of a cell suspension containing preferably human cells to the polymer scaffold; placement of the seeded polymer scaffold in a bioreactor and mechanical stimulation by exposure to a pulsatile flux of incremental intensity, thereby forming an extracellular matrix; mounting of the graft on a conduit stabilizer and incubation in cell culture medium; decellularisation of the graft in a washing solution; nuclease treatment of the graft; and rinsing of graft. The invention further comprises and various steps of quality control of the tissue-engineered medical device.

37 Claims, 18 Drawing Sheets

(51) Int. Cl.
    *A61F 2/24*     (2006.01)
    *A61L 2/20*     (2006.01)
    *A61L 27/34*     (2006.01)
    *A61L 27/38*     (2006.01)
    *B05D 1/18*     (2006.01)
    *A61L 27/50*     (2006.01)

(52) U.S. Cl.
CPC .............. *A61L 27/34* (2013.01); *A61L 27/362* (2013.01); *A61L 27/3604* (2013.01); *A61L 27/3641* (2013.01); *A61L 27/3683* (2013.01); *A61L 27/3687* (2013.01); *A61L 27/3691* (2013.01); *A61L 27/3808* (2013.01); *A61L 27/3834* (2013.01); *A61L 27/507* (2013.01); *B05D 1/18* (2013.01); *C12N 5/0697* (2013.01); *A61L 2202/21* (2013.01); *A61L 2420/02* (2013.01); *A61L 2430/20* (2013.01); *A61L 2430/40* (2013.01); *C12N 2533/40* (2013.01)

(56) References Cited

OTHER PUBLICATIONS

Benedict Weber et al., "Off-the-shelf human decellularized tissue-engineered heart valves in a nonhuman primate model", Biomaterials, 2013, pp. 7269-7280, vol. 34, No. 30, XP028679336.
International Search Report for PCT/EP2018/073076 dated Oct. 9, 2018 [PCT/ISA/210].
Written Opinion for PCT/EP2018/073076 dated Oct. 9, 2018 [PCT/ISA/237].
Bart Sanders et al., "Improved Geometry of Decellularized Tissue Engineered Heart Valves to Prevent Leaflet Retraction" Annals of Biomedical Engineering, vol. 44, No. 4. Apr. 2016, pp. 1061-1071.
Shea, M. J. et al., "The Biology of the heart", MSD Manual Consumer Version, from the Internet Feb. 2017, date search: Jul. 4, 2022 (9 pages total).

* cited by examiner

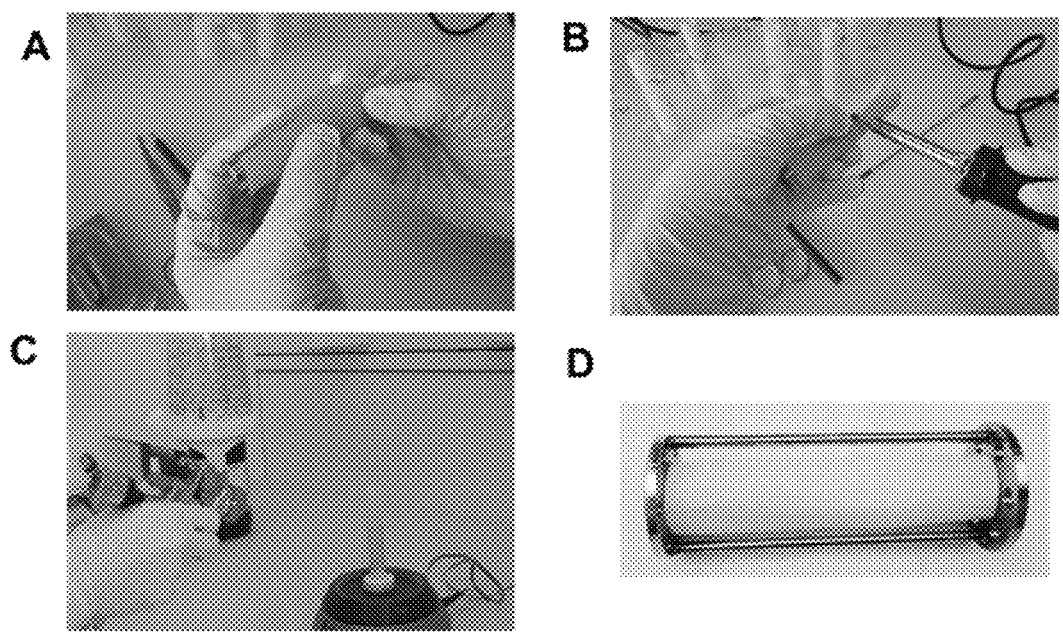
FIG. 2
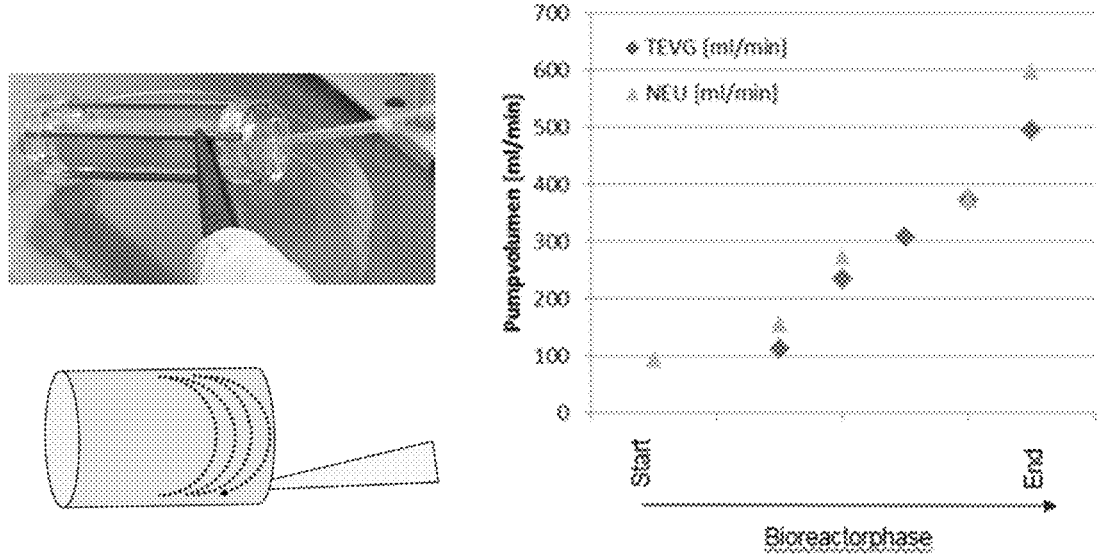
FIG. 3
FIG. 4

| Thresholds of lactate measurement: | |
|---|---|
| Medium change interval | Threshold of lactate measurement [mmol/l] |
| 1 | 1.5 |
| 2 | 2.5 |
| 3 | 3.0 |
| 4 | 3.5 |
| 5 | 3.5 |

FIG. 5

| Step | description | approx duration |
|---|---|---|
| 1 | cool to -40°C at 1°C/min | 60 min |
| 2 | hold (60-)120 min | 60 min |
| 3 | ramp to -20°C | 30 min |
| 4 | hold 60 min | 60 min |
| 5 | ramp to -40°C | 30 min |
| 6 | hold 60 min | 60 min |
| 7 | start vacuum (3-10 Pa) | |
| 8 | ramp to -5°C (after step 7) | 35 min |
| 9 | dry at -5°C and 3-10 Pa for 12 h | 720 Min |
| 10 | ramp to 20°C | 30 min |
| 11 | dry at 20°C and 3-10 Pa for 3 h | 180 min |
| | total | 1265 min |
| | | 21.08 h |

FIG. 6

FIG. 7
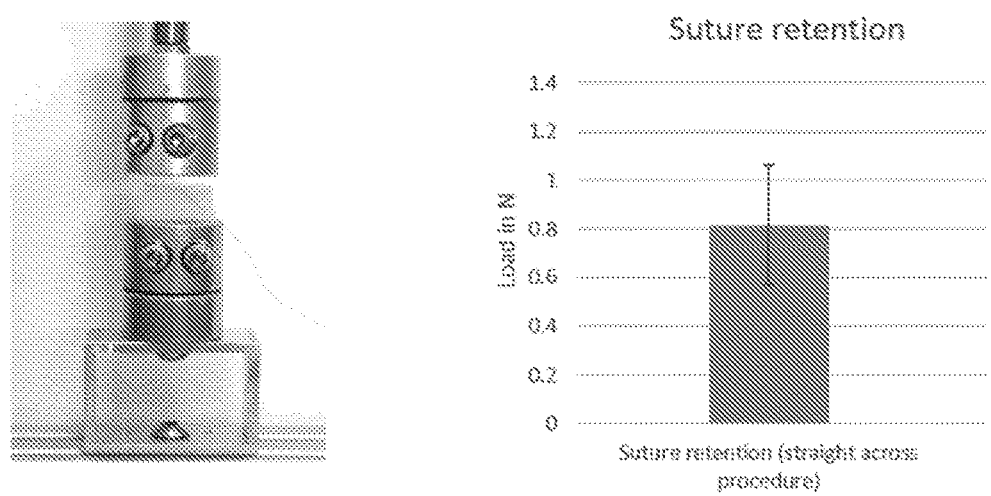
FIG. 8A  FIG. 8B

TISSUE-ENGINEERED MEDICAL DEVICE

TECHNICAL FIELD

The present invention relates to the production of a tissue-engineered medical device for use in therapeutic applications, such as tissue replacement interventions, especially for use in cardiovascular applications. The medical device comprises a hybrid structure of a biodegradable synthetic scaffold and a tissue engineered extracellular matrix grown from human or animal cells.

PRIOR ART

Tissue-engineered constructs are useful as prostheses in the repair or replacement of damaged tissues or even organs. In cardiovascular surgery there is a large need for grafts, patches and valves to replace failing tissues due to congenital disorders or for example calcification and degeneration. Currently used materials for soft tissue repair are either non-degradable synthetic grafts or fixated tissues from allo-/xenogenic origin and therefore inherently associated with progressive dysfunctional degeneration, risk for disease transmission, and lack of regenerative capacity. These drawbacks limit their broader use in younger patient populations or require several reoperations. Non-degradable synthetic polymer constructs bear the risk of infection, calcification, or inflammation following implantation. Degradable synthetic polymers have found a wide use as tissue culture scaffolds, however, fragments of degradable polymers can cause inflammatory reactions. Alternatively, scaffolds of non-human (e.g. bovine or rat) collagen gels or meshes show limited tensile strength and entail the risk of contamination or immunogenic reactions after implant into a human patient.

Biodegradable scaffold matrices are used to form the basis of any in vitro tissue engineering approach by acting as a temporary matrix for cell proliferation and extracellular matrix deposition until the scaffold is replaced by neo-tissue. While the engineered living substitute develops, the biocompatible scaffold should degrade ideally without leaving remnants in the body. PGA is most commonly used because it degrades at predictable time point and into (generally) biocompatible components. Besides, the high porosity of PGA meshes permits a good diffusion, neovascularization and cellular infiltration[2]. Unfortunately, PGA meshes are biodegraded rapidly within few weeks and can therefore not withstand mechanical forces exerted to the materials and guide the shape of the bioengineered construct over longer culturing periods[2,3]. As a result, hybrid polymers have been designed in order to combine the shape-memory and mechanical stability of slowly degrading polymers with the fast degrading properties of polymers, such as PGA[4]. For instance, combinations of PGA with polymers such as (poly-4-hydroxybutyrate) P4HB, PLA, or PGA have been explored [5,6]. Unlike PGA, which is synthetized chemically, P4HB is produced naturally by microorganisms, making it more challenging to be synthesized[7]. After implantation into the body, P4HB degrades mainly by bulk hydrolysis producing 4HB, a normal component of the mammalian body[8]. In 1998, Shinoka et al. reported surgical implantation of tissue engineered vascular grafts in lambs, in which scaffolds were constructed from autologous cells seeded onto PGA grafts[9].

For both heart valve and vascular tissue engineering, the use of PGA meshes coated with P4HB, i.e. the combination of the thermoplastic characteristic of P4HB and the high porosity of PGA meshes, has been investigated intensively with promising results in vitro and in preclinical studies[10-12]. In 2006, Hoerstrup et al. provided the first evidence of living, functional pulmonary arteries engineered from vascular cells seeded on PGA/P4HB scaffolds in a growing lamb model[5].

While preliminary attempts with decellularized xenogeneic and allogeneic grafts have only shown limited host cell repopulation in pre-clinical and clinical trials, the concept of tissue engineered, living, and autologous heart valves with self-repair and remodelling capacity has been proposed as a promising alternative to overcome such limitations.

Following the approach of in vitro tissue engineering, the successful fabrication of autologous living cardiovascular replacements similar to their native counterparts is dependent on three main elements: 1) autologous cells that resemble their native counterparts in phenotype and functionality, 2) a biocompatible temporary supported matrix which promotes tissue strength until the extracellular matrix produced by the autologous cells guarantees functionality on its own, and 3) culture conditions enabling tissue formation and maturation by in vitro conditions similar to a physiological environment, i.e. suitable biochemical (e.g. growth factors) and physical (e.g. cyclic mechanical loading) stimuli supporting tissue formation in vitro and in situ. However, this "classical" tissue engineering concept comprising complex multistep procedures such as cell harvest, cell expansion, seeding on scaffolds, bioreactor in vitro culture, and time-critical implantation coordination of the delicate, living engineered autologous grafts requires high logistical and financial efforts.

Besides a few occasional pilot studies based on decellularised heart valves[14,15], no systemic evidence that the heart valve tissue engineering concept can be applied in the clinical routine has been reported so far.

EP 1 315 796 discloses the production of a tissue engineered artery from cells that are seeded and grown on degradable polymer scaffolds (see also [16]). However, here a biopsy from the intended recipient of the autologous vessel is needed.

Therefore, it is desirable to provide a method to produce a large number of off-the-shelf available tissue-engineered medical devices, especially cardiovascular grafts, which do not require any human or animal biopsy of the intended recipient as a starter material, but are based on a safe, established, controlled, and abundantly available homologous human or animal cell source. Advantageously, the envisaged tissue-engineered medical device shall have a prolonged shelf life time and shall be available in a large variety of sizes and shapes. The envisaged product shall advantageously be completely biodegradable, allow rapid repopulation by the host's cells towards a native-like tissue provide self-repair and regenerative capacity, and importantly be amenable to somatic growth.

SUMMARY OF THE INVENTION

The present invention proposes an innovative approach of producing decellularized homologous tissue-engineered matrices as tissue replacements, especially for cardiovascular applications, wherein the suggested method overcomes the disadvantages of the prior art in that it simplifies and shortens the production process by enabling off-the-shelf availability and reproducibility and in that it minimizes the risk of infection or inflammation and immunologic reactions following the implantation.

Scaffold Production:

The invention concerns a method for the production of a tissue-engineered medical device (TEND), comprising the following steps:

First, a substrate, preferably a mesh comprising polyglycolic acid (PGA), preferably a non-woven PGA-mesh, is provided as a starting material for a polymer scaffold. Alternative materials are possible as long as they offer a comparable porous structure which is necessary for sufficient cell ingrowth. Possibly, a PGA-mesh further comprising poly-Lactic acid (PLA) can also fulfil these requirements.

In a first coating step, the mesh, preferably being a non-woven PGA-mesh, is coated with a first coating solution containing poly-4-hydroxybutyrate (P4HB), which is a type of polyhydroxyalcanoate (PHA). Preferably, the first coating solution is a low-percentage solution of P4HB in an apolar solvent, e.g. tetrahydrofurane (THF), wherein the P4HB content preferably is 0.5%-2%, more preferably about 1%. This first coating step is preferably conducted by dip-coating of the mesh in the first coating solution, however, other coating methods, such as e.g. spray coating, are possible. The biodegradable P4HB conveys mechanical stability in the final product (besides the extracellular matrix, see below), which is necessary to withstand blood pressure right after implantation, while the PGA is degraded to a large extent already during the bioreactor phase, as described below. PLA can serve as an alternative coating of the PGA-mesh.

Following the first coating step, the coated mesh preferably is air-dried for several hours in order for the solvent to evaporate.

In case the tissue-engineered medical device to be produced is a vascular graft (or a vascular graft furthermore comprising a tissue-engineered heart valve grown thereon/therein), the coated mesh, after the first coating step, is then shaped to a tube or hollow cylinder. For this purpose, the mesh is preferably wrapped around a shape giver, e.g. a metallic cylinder with the required dimensions. Subsequently, the edge areas are fixed, preferably by overlapping the two edges and by heating the overlapping edges to at least 60 degrees Celsius, preferably to about 80 degrees Celsius, e.g. using a soldering iron. Thereby, P4HB itself is used as the fusing element, since it is thermoplastic with a melting point of 60 degrees. This has the advantage that the tubular polymer scaffold is composed entirely of biodegradable substances. Alternative methods for fixing the edges of the tube or hollow cylinder include gluing, needling and weaving, as well as intermolecular polymer bonding. The diameter of the tube is variable and therefore adjustable according to the target vessel in which the TEVG is to be implanted (in terms of vessel type and patient size) by choosing different patch sizes of the mesh as a starting material. The desired radial diameter of the tubular polymer scaffold is 1.0-2.5 cm, more preferably 1.2-1.8 cm, most preferably about 1.6 cm, as in the case of a graft for a pediatric cavopulmonary connection.

In the case of a tubular polymer scaffold, a second coating step is carried out: In this second coating step, the tubular polymer scaffold is coated with a preferably low-percentage solution containing P4HB, preferably with a content of 1-3%. more preferably about 2% P4HB. Preferably, the tubular polymer scaffold is coated only on its outer side, which is along the outer (jacket-) surface of the tubular polymer scaffold. For this purpose, the tubular polymer scaffold is preferably mounted on a holding device. This second coating step preferably is carried out by spray coating, preferably with a spraying device such as e.g. an airbrush pistol. This step can be repeated multiple times, according to the desired thickness of the coating. Preferably, in the second coating step, the spray coating of the outer surface of the tubular polymer scaffold is carried out three times. Preferably, the final content of P4HB in the tubular polymer scaffold is 5%-95% (w/w) (weight percent), more preferably 20-50%, even more preferably 22-45%, and most preferably 24-32% (w/w) (weight percent). The content is preferably determined by weighing the scaffold prior to the first coating step and, if applicable, after the second coating step.

Subsequently (whether tubular or not), after coating, the polymer scaffold is sterilized, preferably by ethylene oxide treatment. Alcohol- and/or radiation treatment can be chosen as additional or alternative sterilization steps.

After coating and sterilization, the polymer scaffold is preferably incubated in cell culture medium, preferably for 12-72 hours for equilibration purposes prior to seeding, to facilitate subsequent cell attachment.

A polymer scaffold with the desired porous structure and exhibiting the desired properties (as listed further below for quality control) can be obtained using the above mentioned production and coating method. Furthermore, alternative techniques such as additive manufacturing using said polymers and methods such as FDM (fuse deposition modelling) or Melt Electro Writing can be used to generate polymer scaffolds in said dimensions with the respective structural and topographical properties.

A starter matrix in form of a polymer scaffold of a PGA-mesh coated with P4HB, preferably produced and coated according to the above mentioned steps, can also be readily obtained, i.e. purchased "off the shelf" and used as a substrate for the production of a tissue-engineered medical device.

Cell Isolation, Expansion and Seeding:

In the production of a tissue-engineered medical device according to the present invention, a cell suspension containing isolated and expanded human cells is applied to, i.e. seeded on the polymer scaffold. The production of such a cell suspension, comprising the cells and a cell carrier solution, is described further below.

The cells used for seeding on the polymer scaffold preferably are human cells, preferably selected from a group consisting of fibroblasts, myofibroblasts, mesenchymal stem cells, mononuclear cells, and endothelial progenitor cells. The human cells are preferably derived from a source selected from a group consisting of: bone marrow, blood, adipose tissue, amniotic fluid, chorionic villi, umbilical cord matrix, umbilical cord blood. More preferably, the human cells used for seeding on the polymer scaffold are human fibroblasts, most preferably human fibroblasts derived from human umbilical cord vein (vein tissue). Alternative sources of fibroblasts include but are not limited to foreskin, dermis, aortic-/saphenous vein, peripheral artery, etc. (suitable cell types especially advantageous for heart valve tissue engineering are listed in [17]). Cells from an established cell line can also be used.

As an alternative to human cells, animal cells can be used from equivalent tissue sources for the production of the cell suspension.

Preferably at least 80 million cells, preferably 100-130 million cells, more preferably 115 million+/−12 million cells are seeded on the polymer scaffold within a cell carrier solution. The preferred density of cells on the polymer scaffold is 0.5-5 million cells/cm$^2$, more preferably 2-4 million cells/cm$^2$, most preferably between 2.2.-3.3 million cells/cm$^2$.

As mentioned, it is possible that the cells are purchased, i.e. obtained in an already isolated form. If not obtained or purchased from another source, the provision of cells for seeding the polymer scaffold is preferably also a part of the production method of a tissue-engineered medical device (TEMD) according to a further aspect of the invention. In case the cells first have to be isolated for the purpose of seeding the scaffold, the method of producing a TEMD according to the present invention additionally comprises the isolation of human cells, preferably selected from a group consisting of fibroblasts, mesenchymal stem cells, mononuclear cells, and endothelial progenitor cells, wherein the human cells are preferably derived from a source selected from a group consisting of: bone marrow, blood, adipose tissue, amniotic fluid, chorionic villi, dermis, umbilical cord matrix, umbilical cord blood; The human cells used for seeding the polymer scaffold are preferably selected from a group consisting of:

fibroblasts, preferably derived from one of human umbilical cord vein (vessel wall tissue), dermis, foreskin, aortic vein, saphenous vein, or peripheral artery; more preferably derived from human umbilical cord vein;

mesenchymal stem cells, preferably derived from bone marrow, adipose tissue, amniotic fluid, chorionic villi, umbilical cord matrix or umbilical cord blood;

mononuclear cells, preferably derived from bone marrow;

endothelial progenitor cells, preferably derived from blood, amniotic fluid, or umbilical cord blood;

myofibroblasts, preferably derived from the aorta, the umbilical cord vein, or from other tissue of the umbilical cord (e.g. Wharton's jelly).

Cells are selected by selective medium and adhere to a tissue culture plate. Cells are identified by flow cytometry with suitable cell surface markers. The cells are then left to proliferate, wherein a doubling time of less than 100 hours serves as a preferred quality control criterion, besides the requirement of being pathogen-free. Preferably, homologous cells are used. Unlike the autologous approach, the tissue engineering process is patient independent, hence cell banks can be established and optimal cell sources picked. Optionally, a master cell bank (MCB) can be formed by expanding isolated cells and cryopreserving them in multiple and identical aliquots. In the case of isolation of fibroblasts from the umbilical cord vein, with one umbilical cord biopsy, a MCB can be established that is sufficient to produce roughly 700 TEMD that are available off-the-shelf. In the case of a MCB, a working cell bank (WCB) can be derived from the MCB by thawing an aliquot of desired cells from the MCB and further cultivating and subsequently cryopreserving the cells in multiple and identical aliquots to establish a working cell bank.

Whether purchased, taken from an established cell line, or isolated in the course of production of the TEMD according to the present invention, the isolated cells are used for the production of a cell suspension.

In any case, the isolated human cells must be expanded, preferably in culture vessels for preferably 5-8 days.

Preferably cells of a low passage number (preferably earlier than P5, more preferably earlier than P3) are harvested and used for seeding onto the polymer scaffold, in order to minimize the risk of loss of the differentiated phenotype of the cells. After reaching a sufficient number of cells in culture to seed 70-180 million cells, preferably 100-130 million cells, most preferably about 115 million cells per medical device (graft), the expanded human cells are harvested. Preferably, between $20\times10^6$ cells/ml and $60\times10^6$ cells/ml, more preferably between $35\times10^6$ cells/ml and $45\times10^6$ cells/ml, and most preferably about $41\times10^6$ cells/ml are used for seeding on the polymer scaffold.

The harvested cells are used to form a cell suspension by adding a cell carrier solution, preferably comprising a gelling agent, to the isolated human cells. The cell carrier solution preferably contains purified thrombin and purified fibrinogen. Preferably, the cell suspension is formed by first adding purified fibrinogen to the isolated human cells to form a first cell suspension, and in a second step adding purified thrombin to the first cell suspension to form a second cell suspension for seeding on the polymer scaffold. Immediately after addition of thrombin, coagulation occurs, which results in an attachment of the cells to the polymer scaffold. The preferred coagulation time of the cell suspension after addition of the cell carrier solution is 5-8 min, which is preferably controlled prior to seeding the cell suspension on the polymer scaffold.

In the case of a tubular polymer scaffold, such as for the production of a tissue-engineered vascular graft, preferably, the cell suspension, the production of which is described below, is applied/seeded only on to an inner surface of the tubular polymer scaffold. For this purpose, the cells are seeded in a homogenous manner along the inner surface of the tubular polymer scaffold, which is formed as a hollow cylinder, resulting in a homologous distribution of the cell suspension on the substrate. A homologous seeding of the cells can also be achieved in that the tubular polymer scaffold is temporarily sealed at the open ends, filled with a cell suspension and subsequently rotated in a cylindrical container filled with cell culture medium.

After seeding and prior to incubation in the bioreactor, the seeded polymer scaffold is preferably incubated at static conditions for 12-48 hours, more preferably for 16-24 hours, in the same cell culture medium as in the bioreactor phase as mentioned below.

Bioreactor Phase:

After seeding the cell suspension on the polymer scaffold, the method of producing a TEMD according to the present invention comprises the following steps:

The seeded polymer scaffold is placed in a bioreactor and mechanically stimulated by exposure to a pulsatile flux of incremental intensity. Preferably, the mechanical stimulation during this "conditioning step" is carried out over 10-30 days, preferably over 15-25 days, most preferably over 16-20 days. If the duration of stay in the bioreactor is too short, insufficient tissue is developed, if the duration of stay is too long, the conduit starts contracting (visual control). Preferably, the culture medium contains ascorbic acid, i.e. Vitamin C, preferably about 0.0225% v/v (volume/volume), wherein more preferably, the culture medium in the bioreactor is the same as the culture medium used during cell expansion, with the exception that ascorbic acid is added. According to a preferred embodiment of the inventive method, the culture medium inside the bioreactor is changed in defined intervals, preferably twice a week. The result of this bioreactor phase, in which the seeded scaffold is trained or conditioned to withstand physiological conditions, is the inventive tissue-engineered medical device. During the presence of the TEMD in the bioreactor, an extracellular matrix (ECM) is formed. The cell performance and therefore ECM-formation on the TEMD is monitored during the bioreactor phase. For this purpose, as listed further below, the medium composition and lactate values are controlled.

Subsequently, the TEMD is removed from the bioreactor. After removal of the TEMD from the bioreactor, the TEMD is mounted on a stabilizer. In the case of a TEMD based on a tubular polymer scaffold, the stabilizer is a conduit stabilizer which preferably has a cylindrical shape. During the bioreactor phase the TEMD has the tendency to contract, most likely due to formation of ECM. The mounting on the stabilizer is therefore useful to re-establish the original shape of the TEMD after possible "shrinkage" during the conditioning phase in the bioreactor. The TEMD is then incubated, preferably while on the stabilizer, under static conditions, preferably for 12-36 hours, in cell culture medium, wherein the cell culture medium preferably has the same composition as in the bioreactor.

Decellularization, Nuclease Treatment and Rinsing:

After re-shaping, the TEMD is decellularised. During decellularization, the cells are lysed and removed using a washing solution comprising a detergent, such as e.g. Triton-X. Preferably, the washing solution contains phosphate buffered saline (PBS), ethylenediaminetetraacetic acid (EDTA), Triton X-100, and sodium-deoxycholate. More preferably, the washing solution contains PBS, 0.68 mM EDTA, 0.25% (v/v) Triton X-100, and 0.25% (w/w) sodium-deoxycholate. The stringency of the washing solution is chosen in a way that soluble and unwanted cellular components are removed while the extracellular matrix that had been generated by the cells during the bioreactor phase is preserved.

Subsequently, the TEMD is submitted to a nuclease treatment. This enzymatic digestion serves to remove DNA from the TEMD. For this purpose, an endonuclease or an exonuclease can be used. Preferably, benzonase is used for the DNA digestion. To ensure that only minimal remnants of DNA remain, a quality control step of determination of residual DNA content is performed on the finished product as described below.

The decellularization and nuclease treatment steps offer the advantages that firstly, immunogenicity is reduced, as homologous cells are used for production of the TEMD. Secondly, since no living cells remain on the final TEMD, the final product can be sterilized, which is beneficial for the patient, as it reduces the risk of infection. Thirdly, the final product can be lyophilized, packed and stored and therefore provided in an "off the shelf" manner.

In a final step of producing a TEMD according to the present invention, the TEMD is rinsed in a rinsing solution, preferably in PBS, and then in deionized water ($ddH_2O$), to remove salts. The TEMD is then preferably transferred to a tube with a filter cap for postponed use.

Lyophilisation, Packaging and Sterilization:

Following the rinsing of the TEMD, the method according to the present invention preferably comprises at least one, and more preferably all of the following steps:

In order to remove water from the TEMD, i.e. to dry the TEMD, the TEMD is subjected to a lyophilisation treatment, i.e. freeze drying. For this purpose, the TEMD is preferably lyophilized in a closed tube with a filter lid in order to reduce the risk of contamination.

An optimal lyophilisation program is necessary in order to prevent damaging of the material, e.g. due to crystal formation. The lyophilization is preferably conducted according to a program according to FIG. 6. Lyophilization allows storage of the TEMD in a completely dried state, making banking and transport easier.

Furthermore, the TEMD is packaged. Preferably, in order to sufficiently protect the TEMD from mechanical damage, contamination and liquid or humidity, the lyophilized TEMD is double packaged, e.g. in a sterilization bag, tube, blister packaging, etc.

Finally, the TEMD is subjected to a sterilization step, which is preferably realized by ethylene oxide treatment. This is easier if the product has been lyophilized, as ethylene oxide could react with water. Alternative sterilization treatments include ethanol treatment. However, this more aggressive form of treatment is more likely to damage the material.

In-Process Quality Control:

Several quality control steps are carried out during the production process of the TEMD. Therefore, according to a further aspect of the present invention, the method for the production of a TEMD further comprises at least one, preferably at least two, more preferably all of the following in-process steps:

Measurement of a content of P4HB in the polymer scaffold: Preferably the content of P4HB in the polymer scaffold is in the range of 20-50% (w/w), more preferably 22-45%, most preferably 24-32%. For this purpose, the PGA-mesh is weighed prior to the first coating step and then after the first or after the second coating step, if applicable, and the two weight values are compared to each other.

Ensuring of homologous deposition of P4HB on the mesh during the first coating step, and then also during the second coating step (if applicable): This is ensured by visual control during each coating step.

Examination of human cells to be seeded on the polymer scaffold, preferably in terms of cell identity and/or proliferation and/or viability, and/or lack of pathogens: Cell identity (phenotyping) is preferably verified via flow cytometry, using FACS-analysis with various cell surface markers. The acceptance criteria include, but are not limited to a content of at least 80% of CD90-positive and CD26-positive cells, and 5% or less of CD90-negative and CD31-positive cells. As an alternative to FACS-analysis, microarray can be used.

Viability and proliferation: This is verified by measuring the doubling time. Preferably, the doubling time is less than 100 hours. The preferred maximal passage number of cells used for seeding on the polymer scaffold is P3.

Furthermore, the cells must be verified to be free of pathogens (below the limit of detection (LOD)).

Control of the coagulation time during the preparation of the cell suspension: This is preferably conducted by controlling the amount of the gelling agent. When using a combination of thrombin and fibrinogen, a ratio of 1:1 is preferred (unit: mg). The acceptance criterion for the coagulation time preferably is 5-8 minutes;

Control of the number of human cells seeded on the polymer scaffold: The preferred number of cells seeded shall be between 2-4 million cells per $cm^2$, preferably between 2.3-3.3 million cells per $cm^2$ of the polymer scaffold surface area.

Control of homogenous application of the human cells to the polymer scaffold: this is carried out by visual control.

Control of medium composition during the bioreactor phase (see below): The Vitamin C content preferably is 0.0225% (v/v) in the medium. The preferred composition of the medium in the bioreactor is as follows: 500 ml A-DMEM (Advanced-Dulbecco's Modified Eagle Medium), 50 ml Fetal Bovine Serum (FBS) (resulting in 9% (v/v)), 5 ml Glutamax (200 mM) (resulting in 1.8 mM), 0.5 ml Gentamycin (10 mg/ml) (resulting in 0.009 mg/ml), 0.63 ml Vitamin C (20%) (resulting in 0.225% (v/v)).

Control of cell performance during the bioreactor phase: Lactate is used as a preferred marker for cell performance during the bioreactor phase. For this purpose, the lactate value is controlled at each medium change. Lactate values should be at least 1.5 mmol/l at the first medium change, at least 2.5 mmol/l at the second medium change, at least 3.0 mmol/l at the third medium change, at least 3.5 mmol/l at the fourth and fifth medium change.

Control of ECM formation during the bioreactor phase: The ECM-formation during the bioreactor phase can be verified, for example, by mass spectrometry (MassSpec). Human Procollagen Type I C-Terminal Propeptide is split off during ECM production and is released into the medium by the cells. Therefore, this propeptide can be detected in the medium during the bioreactor phase and can be used as a suitable marker for ECM formation.

The verification of ECM formation is conducted after the incubation of the TEMD on the stabilizer in a lyophilized, dried state.

Post-Production Quality Control of the TEMD:

Furthermore, preferably the finished TEMD, i.e. the end product, is subjected to a quality control comprising at least one, preferably more than one, more preferably all of the following steps:

Verification of sterility: The implantation of the TEMD into the intended recipient patient must be carried out under sterile conditions. The sterility of TEMD samples from a specific batch verifies that the sterilization during the production process is reliable and reproducible.

Measurement of endotoxin content: The acceptance criterion for the amount of endotoxin is <0.29 EU/ml, which corresponds to <0.29 EU/Patch ("EU"=endotoxin units, "Patch"=biopsy punch with a diameter of 8 mm and an area of 0.5 cm$^2$). Endotoxins are heat-stable components of the outer cell membrane of bacteria. A presence of endotoxins in the end product would be an indication for bacterial contamination in the process and would jeopardize the health of patients in clinical trials. The test is determined to verify the absence of any such bacterial remnants in the end product.

Measurement of mycoplasma content: Mycoplasma are very small bacteria which can appear as contaminants in cell cultures. As mycoplasma are not detectable by light microscopy and in some cases are resistant against standard antibiotics, they often remain undetected and influence or impair the growth of the respective cell culture. A mycoplasma contamination of human cell culture used for the seeding of the TEMD could also lead to a contamination of the end product. In order to verify that the production process is reliable and reproducibly free of any such contamination (below the limit of detection (LOD)), the conduit samples are tested by quantitative real-time Polymerase Chain Reaction (qPCR) for the presence of mycoplasma. The LOD of qPCR is described in Ph. Eur. 2.6.7 as 1000 GC Mycoplasma DNA concentration per vascular graft.

Measurement of residual DNA content: Remaining DNA on the TEMD could be a danger to the health or even life-threatening for the intended recipient. The DNA-content in the conduit samples of different batches is determined by qPCR in order to verify that the removal of DNA is carried out in a reliable and reproducible manner. Therefore, a preferred acceptance criterion for a residual DNA content is less than 50 ng dsDNA per mg dry weight.

Measurement of residual water content: In order to prevent the hydrolytic degradation and therefore to prolong the shelf life of the final product, the TEMD is lyophilised (freeze-dried) after the decellularization step. The determination of the water content in the TEMD samples of different batches is carried out to verify that the lyophilisation in the production process is reliable and reproducible. Preferably, the residual water content is less than 5%.

Measurement of polymer content: The polymer analysis allows to determine whether the content, ratio and/or the molecule size (chain length) of the polymers are constant across various batches of TEMD produced by the method according to the present invention. Preferably, the finished, decellularized TEMD has a content of 20-75% (w/w) P4HB, more preferably of 30-60% (w/w) P4HB, most preferably of 40-50% P4HB, and preferably 0-30% of PGA, more preferably 10-20% of PGA, most preferably 15-18% of PGA.

Measurement of hydroxyprolin content: Collagen is an important structural component in ECM-tissue of the final TEMD according to the present invention. Contrary to other proteins, collagen contains the amino acid hydroxyprolin (HYP). The collagen content can therefore be measured by quantifying the HYP-content in TEMD of various batches. This should ensure a reliable and reproducible ECM-production during the production process across various batches. A preferred acceptance criterion for the hydroxyprolin content is more than 5 µg/mg.

Measurement of protein content by various ECM marker proteins, wherein preferably, the content of the following proteins is determined: fibronectin, collagen alpha-2(I) chain, collagen alpha-2(VI) chain. Furthermore, preferably the protein content of various decell-markers is determined, preferably as follows: superoxide dismutase; 60S acidic ribosomal protein P2; integrin alpha 5. The final TEMD product comprises a characteristic distribution of proteins. Desired and/or undesired proteins are quantified by mass spectrometry analysis (LC-MS/MS) of the peptides and the use of specific reference peptides. The detection of the desired proteins, i.e. ECM-markers, is representative via the determination of the peptide fragments of three highly abundant proteins: fibronectin, collagen alpha-2(I) chain, collagen alpha-2(VI) chain. By means of this measurement, the content of these structural ECM-proteins is verified to be constant and reproducible across various batches of TEMD. The acceptance criterion for the content of said ECM-proteins are: a content of fibronectin of at least 100 fmol/µg, and/or a content of collagen alpha-2(I) chain of at least 200 fmol/µg, and/or a content of collagen alpha-2(VI) chain of at least 5 fmol/µg.

The content of undesired proteins, i.e. decell-markers, is determined in that the following representative non-ECM proteins and/or their peptide fragments are quantified: superoxide dismutase, 60S acidic ribosomal protein P2, Integrin alpha-5. By means of this measurement, in which the content of these proteins should be below a specific threshold value, it is shown that the decellularisation was successful. This allows to verify a constant and reproducible decellularisation. The acceptance criterion for the content of said decellularisation marker proteins are: a content of superoxide dismutase of less than 3 fmol/µg, preferably of less than 2 fmol/µg, and/or a content of 60S acidic ribosomal protein P2 of less than 3 fmol/µg, preferably of less than 2 fmol/µg, and/or a content of integrin alpha-5 of less than 3 fmol/µg, preferably of less than 2 fmol/µg.

For the above mentioned quality control steps, the samples are analysed in a dried form after lyophilisation.

For following biomechanical tests, the samples are rehydrated. The material thickness is measured in a lyophilized state and after rehydration:

The wall thickness of the TEMD is preferably measured by microscopic analysis. The preferred acceptance criterion for the wall thickness is 0.1-20 mm, preferably 0.1-0.6 mm in dry form and/or of 0.15-25 mm, preferably 0.15-0.7 mm in rehydrated form, respectively, and more preferably 0.3-0.4 mm in the dry form and/or 0.35-0.5 mm in the rehydrated form, respectively. The wall thickness is critical for the mechanical stability of the TEMD, especially when the TEMD is a vascular graft. The thickness of TEMD samples of various batches was determined in order to verify that the end products had a constant and reproducible required minimum wall thickness. The wall thickness of the TEMD according to the present invention was measured in the dry as well as in the rehydrated state. The microscopic analysis of the thickness was carried out on TEMD samples which were subsequently submitted to a suture retention or tensile strength test (see below).

To test the mechanical loading capacity of the TEMD, a suture retention test is preferably carried out. The suture retention test, in which the strength necessary to tear out a thread from a seam in the TEMD, serves to analyse the mechanical strain, which the TEMD is submitted to when implanted into a patient. It is thereby verified that a TEMD produced according to the inventive method is able to resist the required minimum strain in a reproducible manner. The preferred acceptance criterion for the suture retention is at least 0.5 N.

A further mechanical strain test used on the TEMD is the tensile strength test. Therein, a TEMD-sample is mounted in a draw gear/pulling tool and stretched until the material tears and therefore the maximal tensile strain can be determined. The tensile strength test on TEMD-samples of various batches verifies that the production method yields end products which reproducibly withstand the required minimum tensile strain. The preferred acceptance criterion for the tensile strength of a TEMD according to the present invention is 0.5 MPa.

By carrying out the mentioned quality control steps, the production can be controlled at various steps along the process (in-process and post-production). This allows the process to be conducted in a reproducible and reliable way. Therefore, for quality control, it is possible to conduct random testing of representative samples of the same batch.

With the method described above, a superior tissue-engineered medical device is produced, which comprises a hybrid structure of a synthetic biodegradable polymer scaffold and biologic material. The implantation of a resulting tissue-engineered medical device allows adaptive cell-based remodeling/repopulation in the recipient body towards a functional/physiological native-like tissue structure. What is surprising is that the TEMD according to the present invention provides an optimized intermediate state of engineered tissue maturation, as compared to synthetic polymer scaffolds on the one hand, and mature, decellularized native structures on the other hand. This "controlled immaturity" results in a specific composition/ratio of synthetic components, biological "neo-tissue" and 3D architecture (i.e. porosity, layering) and has advantageous effects, including an increased degree of ingrowth of cells in the recipient body, thereby providing a great asset over grafts produced according to methods of the prior art.

The present invention furthermore concerns a TEMD produced according to the method described above. Preferably, the tissue-engineered medical device is selected from the group comprising: a vascular graft, a valvular replacement (such as a tri-leaflet heart valve, i.e. a sinus valve) or a tissue patch. The tissue patch preferably is an augmentation patch, a septal wall patch or a pulmonary/aortic wall patch. However, alternative uses such as for the replacement of a patch or a lining of a tissue in various organs of the human or animal body are possible. For example, a patch may also serve as a skin graft.

Furthermore, the present invention concerns the use of a TEMD according to the above description, for the treatment of a disease in a human or animal patient, preferably a human pediatric patient. The disease to be treated can be a cardiovascular congenital defect or a heart valve defect. In case of a heart valve defect, the TEMD according to the invention can be designed as a replacement for a tricuspid valve, an aortic valve, a mitral valve or a pulmonary valve. In the setting of congenital cardiovascular defects, the TEMD can be used for reconstructive surgery such as a cavopulmonary connection in a Fontan procedure or correction of any other structural defects (i.e. septal or ventricular defects, reconstruction of the great vessels, etc.).

Another subject of the invention is a method for treating a disease comprising a tissue defect as mentioned above, comprising the implantation of a TEMD according to the above description as a replacement graft. The TEMD according to the present invention can be used in the treatment of a cardiovascular disease in a human or animal patient, comprising the implantation of a tissue-engineered medical device according to one of the above described embodiments in a human or animal body. Preferably, the present invention concerns a method of treating a disease comprising a defect of a cavopulmonary connection in a human or animal patient, the method comprising the implantation of a tissue-engineered medical device according to one of the above described embodiments in a preferably pediatric human or animal body.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 2 shows pictures of the fabrication process of a tubular polymer scaffold for the production of a tissue-engineered medical device according to a first preferred embodiment in the form of a tissue-engineered vascular graft (TEVG), wherein in A, the forming of the mesh into a tube is shown; in B, the fusion of the overlapping edges is shown; in C, the spray coating of the tubular polymer scaffold is shown; and in D, the final tubular polymer scaffold on a mount prior to sterilization;

FIG. 3 shows the seeding of the human cells on the inner surface of the tubular polymer scaffold of FIG. 2;

FIG. 4 shows specifications for a pump flow program for the bioreactor phase;

FIG. 5 shows thresholds of lactate measurement as a marker for cell performance during the bioreactor phase;

FIG. 6 shows the details of the lyophilisation program preferably used;

FIG. 7 shows the results of a material thickness analysis of a TEVG;

FIG. 8 shows in A, a setup used for the suture retention test, and in B, the suture retention strength measured for the final TEVG;

DESCRIPTION OF PREFERRED EMBODIMENTS

Figure 1:
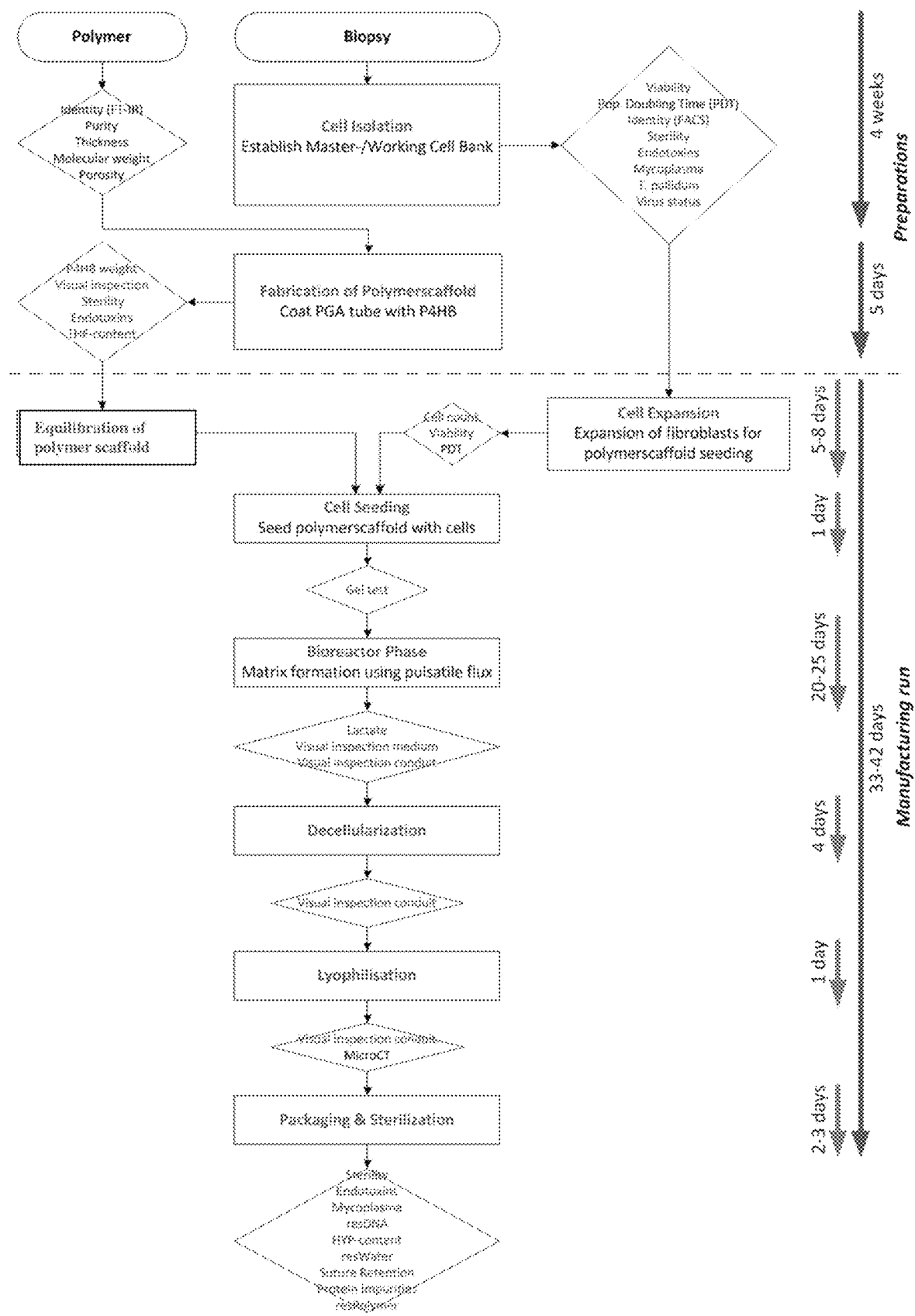
FIG. 1 shows a systematic process overview of the production method according to the present invention, including various quality control steps.

In FIG. 1, the systematic process overview shows the process steps for producing a polymer scaffold and isolating cells as preparatory processes. The products of these preparatory processes, i.e. the polymer scaffold and/or the isolated cells, can individually either be prepared as part of the inventive method of production of the TEMD, as further described below, or separately can be purchased or obtained otherwise for use in the method of production of the TEMD starting with the equilibration of the polymer scaffold and the expansion of the isolated cells to prepare both for the cell seeding step.

Example 1: Production of a Tissue-Engineered Vascular Graft

Isolation and Expansion of Cells:

Human umbilical cords (n=3) were collected after full-term births with informed consent according to the cantonal ethics commission of Zurich, Switzerland [KEK-ZH-2009-0095] and processed for isolation of venous fibroblasts according to established protocols[13]. The umbilical cord vein was isolated surgically and small tissue pieces were cut out using a dissecting scissors. Tissue pieces were placed on a sterile petri dish and were left to adhere to the bottom for 30+/−5 min. Culture medium was gently added and changed every third or fourth day. The preferred medium composition used for the first expansion of the isolated cells is as follows: 500 ml A-DMEM (Advanced-Dulbecco's Modified Eagle Medium), 50 ml. Fetal Bovine Serum (FBS), 5 ml Glutamax (200 mM), 1.25 ml Gentamycin (10 mg/ml). Tissue pieces were removed after first cellular outgrowth after approximately 1-2 weeks of incubation under humidified incubator conditions at 5% $CO_2$ at 37° C.

Scaffold Fabrication:

FIG. 2, which relates to the production of a vascular graft (or a vascular graft comprising a valvular graft attached thereto/therein) according to a first exemplary embodiment of the present invention, shows the forming and soldering of a tubular polymer scaffold after the first coating step (not depicted) as well as the second coating step and the fixation of the tubular polymer scaffold on a mount. The scaffold substrates (scaffold patches) were fabricated from non-woven polyglycolic acid (PGA) meshes (specific gravity 60-80 mg/cm$^3$; Confluent Medical Technologies, Warkwick, USA). The scaffold patches used had a rectangular shape of originally 6 cm×9 cm. Each PGA-mesh was coated in a defined two-step procedure. First, the PGA-mesh was dipped in a low-percentage solution of P4HB (1% poly-4-hydroxybutyrate (P4HB; TEPHA, Inc., USA) in a solution with the apolar solvent tetrahydrofuran (Sigma-Aldrich, Switzerland)) and the solvent was left to evaporate by air-drying for several hours. Next, the PGA-mesh was shaped to a tube by wrapping the mesh around a metallic cylinder with the required dimensions, i.e. radial diameter of 1.6 cm. The overlapping parts/edges of the coated PGA-mesh were fused by heating them to 80 degrees Celsius using a soldering-iron. The tube was then mounted on a holding device and coated on the outside with a low-percentage solution of P4HB (2% in tetrahydrofuran) by using a spraying device (airbrush pistol) in several steps. After the second coating step, the tubular polymer scaffold was shortened to a length of 8 cm (to adapt the size of the tubular polymer scaffold to the size of the holding device later used for placement in the bioreactor). The final composition of the polymer scaffold, i.e. the ratio of PGA to P4HB was determined by weighing of the polymer scaffold before and after coating with P4HB.

The scaffold production steps are applicable to the production of all kinds of TEMD, however, the tube forming step is carried out only in case of the production of a vascular graft (or of a valvular graft if it is to be attached to or in the lumen of a vascular graft). The second coating step is advantageous for tubular scaffolds, and optional for non-tubular scaffolds, such as planar patches or grafts comprising only the valve replacement without any vessel-like portion. Accordingly, the P4HB coating is generally thinner on grafts which were only coated once instead of twice.

The polymer scaffold was then packaged and ethylene oxide sterilized in 6±1% Ethylene oxide and 94±1% $CO_2$ for 180 min at 45±3° C., ≥40% rel. humidity and 2.6±0.1 bar to obtain sterility. Sterilization was followed by an appropriate desorption/ventilation phase to remove residual ethylene oxide from the scaffold.

Prior to seeding, the scaffold was equilibrated by pre-incubation for 12-72 hours in a cell culture medium enriched with ascorbic acid (vitamin C), having the following composition: 500 ml A-DMEM (Advanced-Dulbecco's Modified Eagle Medium), 50 ml Fetal Bovine Serum (FBS) (resulting in 9% (v/v)), 5 ml Glutamax (200 mM) (resulting in 1.8 mM), 0.5 ml Gentamycin (10 mg/ml) (resulting in 0.009 mg/ml), 0.63 ml Vitamin C (20%) (resulting in 0.225% (v/v)).

The porosity of a sample polymer scaffold (DC16-90) was analyzed by Gas Adsorption analysis, i.e. the Brunauer-Emmett-Teller (BET) method, which applies to systems of multi-layer adsorption: Thereby, an average pore radius (BET) of 50 Angström was measured, at a specific surface area of 12 $m^2/g$, and a total pore volume of 0.03 $cm^3/g$.

Cell Seeding:

After pre-incubation/equilibration of the polymer scaffold, the isolated human fibroblasts were seeded onto scaffolds using a density of 2.2.-3.3 million cells/$cm^2$.

For this purpose, the cells were first suspended in purified fibrinogen (Sigma-Aldrich, Switzerland) (10 mg/mL of active protein), followed by addition of purified thrombin (Sigma-Aldrich, Switzerland). Per scaffold, 1.2 mg of fibrinogen and 1.2 U (units) of thrombin were used (ratio of 1:1), resulting in an optimal clotting time of approximately 5-8 minutes. Immediately after coagulation, the cell suspension was seeded onto the sterile scaffolds in a homogenous manner.

In FIG. 3, a preferred pattern of application/seeding of the cell suspension on the inner (lumen-) cylindrical surface of a tubular polymer scaffold is shown. For this purpose, the mount was manually fixed with one hand and the other hand homogenously seeded the cell suspension on the inner surface of the mesh. Other patterns that achieve the desired homogenous distribution of cells are possible. The seeding steps are applicable to the production of all kinds of TEMD.

After seeding, the seeded polymer scaffold was first incubated at static conditions for about 16 hours in the same cell culture medium as mentioned above, also enriched by addition of ascorbic acid (Vitamin C) as follows: 500 ml A-DMEM (Advanced-Dulbecco's Modified Eagle Medium), 50 ml Fetal Bovine Serum (FBS) (resulting in 9% (v/v)), 5 ml Glutamax (200 mM) (resulting in 1.8 mM), 0.5 ml Gentamycin (10 mg/ml) (resulting in 0.009 mg/ml), 0.63 ml Vitamin C (20%) (resulting in 0.225% (v/v)).

Conditioning in Bioreactor:

The seeded polymer scaffold was then placed on a holding device in a bioreactor and exposed to a pulsatile flux of incremental intensity over the next 21+/−4 days in the same above mentioned cell culture medium enriched by addition of ascorbic acid (Vitamin C). The conditioning during the bioreactor phase is applicable to the production of all kinds of TEMD.

In FIG. 4, the specifications for a preferred pump flow program for a TEMD, especially for a TEVG are depicted, showing the generation of pulsatile flow by incremental increase of pumped volume during the bioreactor phase.

FIG. 5 shows a table with minimum thresholds of lactate content in mmol/l at each medium change interval. Lactate serves as a marker for cell performance during the bioreactor phase. During the bioreactor phase, the ECM formation was verified by mass spectrometry, using Human Procollagen Type I C-Terminal Propeptide as a marker in the cell culture medium.

After removal from the bioreactor, the TEVG of Example 1 was placed on a conduit stabilizer and incubated under static conditions for 12-36 hours in the same cell culture medium as in the bioreactor. This step is applicable also to the production of other types of TEMD.

Decellularization:

After incubation, the TEVG of Example 1 was decellularized. During decellularization, cells were lysed and removed using a washing solution that is composed as follows:

| Components | Amount/Volume | Final Concentration |
| --- | --- | --- |
| PBS | 1000 ml | |
| EDTA (0.5M) | 1.36 ml | 0.68 mM |
| Triton X-100 (100%) | 2.5 ml | 0.25% v/v |
| Sodium-deoxycholate | 2.5 g | 0.25% w/v |

In a further step, the decellularized TEVG of Example 1 was treated with the nuclease benzonase in order to remove the DNA by enzymatic digestion. Prior to lyophilisation, the decellularized TEVG was rinsed in dd$H_2O$ to remove salts, cut to a length of 7 cm, and subsequently transferred to a 50 ml tube with a filter cap and then lyophilized (freeze dried). This decellularization step is applicable also to the production of other types of TEMD.

Lyophilization:

In FIG. 6, a preferred program for lyophilisation is depicted. This program prevents damaging of the material, e.g. due to crystal formation. The final product was double packaged in sterilization bags and sterilized by ethylene oxide treatment at an external company (QMedics). This lyophilisation step is applicable also to the production of other types of TEMD.

Quality Control of TEVG:

The final product, i.e. the decellularized, lyophilized and sterilized TEVG, was subjected to a quality control according to the following steps: verification of sterility; verification of endotoxin content; verification of mycoplasma content; verification of residual DNA; verification of residual water content; verification of polymer content; verification of hydroxyprolin content; verification of protein content: fibronectin, collagen alpha-2(I) chain, collagen alpha-2(VI)

chain, decell-markers (superoxide dismutase, 60S acidic ribosomal protein P2, integrin alpha 5); measurement of thickness by microscopic analysis (dry/rehydrated); suture retention test; tensile strength test. These quality control steps are applicable also to the production of other types of TEMDs.

A production batch of TEVG consisted of 6 grafts. One of them was cut apart for the production of representative samples and the pieces were separately packaged, lyophilized, and sterilized, parallel to the remaining 5 grafts. The pieces were then used for the various analyses, including sterility. For the purpose of testing, the packaging was removed again. The TEVG samples were analysed in a dried form after lyophilisation. For the biomechanical tests, the samples were rehydrated.

The wall thickness of the TEVG was determined in a lyophilized state and after rehydration by a measuring microscope (Vision Engineering, HAWK 15-3) according ISO7198:2016 at Endolab Mechanical Engineering GmbH, Thansau/Rosenheim, Germany. Analysis of seven TEVG revealed an average thickness of 342+/−57 μm, as shown in FIG. 7. After rehydration for 20 minutes in 0.9% NaCl the wall thickness increased to by 16% to 397+/−64 μm. The measurement of wall thickness is applicable also to the production of other types of TEMDs.

Figure 9A:
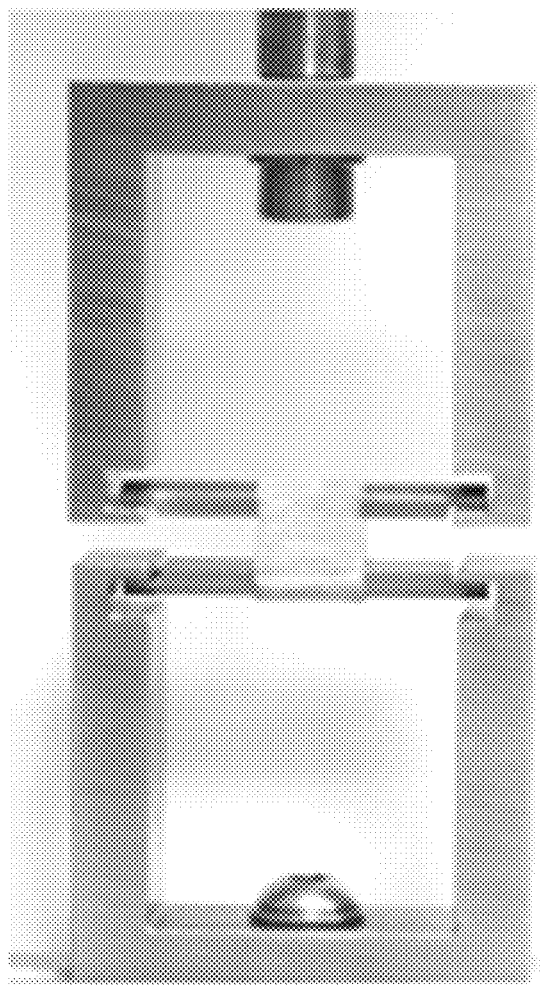
FIG. 9 shows in A, a setup used for the circumferential tensile strength test, in B, raw graphs of the circumferential tensile test, and in C, the circumferential tensile strength of the final TEVG indicated in MPa.
Figure 9B:
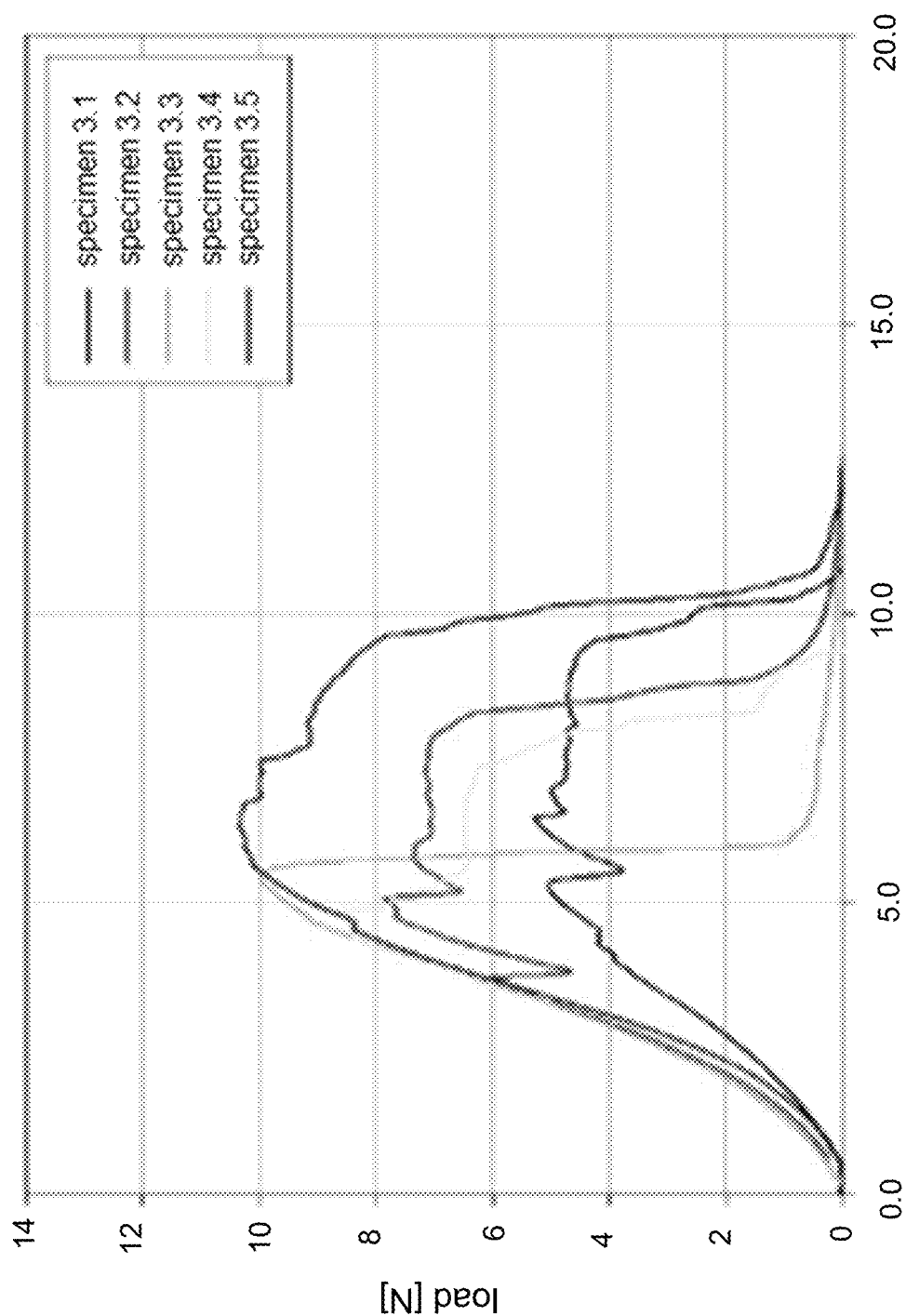
Figure 9C:
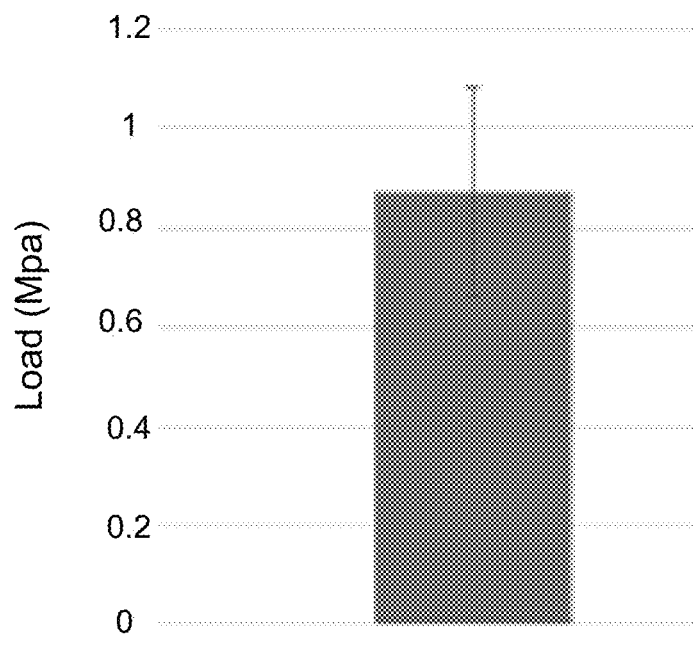

To assess further mechanical properties of a TEMD produced according to the method of the present invention, the circumferential tensile strength of the TEVG produced according to Example 1 was evaluated by using a tensile testing machine meeting the ISO 5081 requirements (Equipment used: Load cell, Instron, 2530-437; Universal testing machine, Instron, 5944). A sample of the final TEVG was cut normal to the long axis and the length of the sample (L) was measured. For the biomechanical analysis the sample was rehydrated for 20 min in 0.9% NaCl solution. The TEVG sample in its tubular form was placed onto two rounded pins (see FIG. 9A). The sample was stretched at a uniform rate of 100 mm/min until the break point was reached. The load at break was determined ($T_{max}$) and the Circumferential Tensile Strength determined by the following formula: Circumferential tensile strength=$T_{max}/2*L$. Tubular TEVG samples (n=5 of 3 different production runs) with an average length of 1.4 cm broke at an average load of 8.4 N, resulting in a circumferential strength of 0.29+/−0.05 N/mm. Based on the wall thickness of the samples a mean circumferential tensile strength of 0.87+/−0.21 MPa was calculated (See FIG. 9C).

Figure 10A:
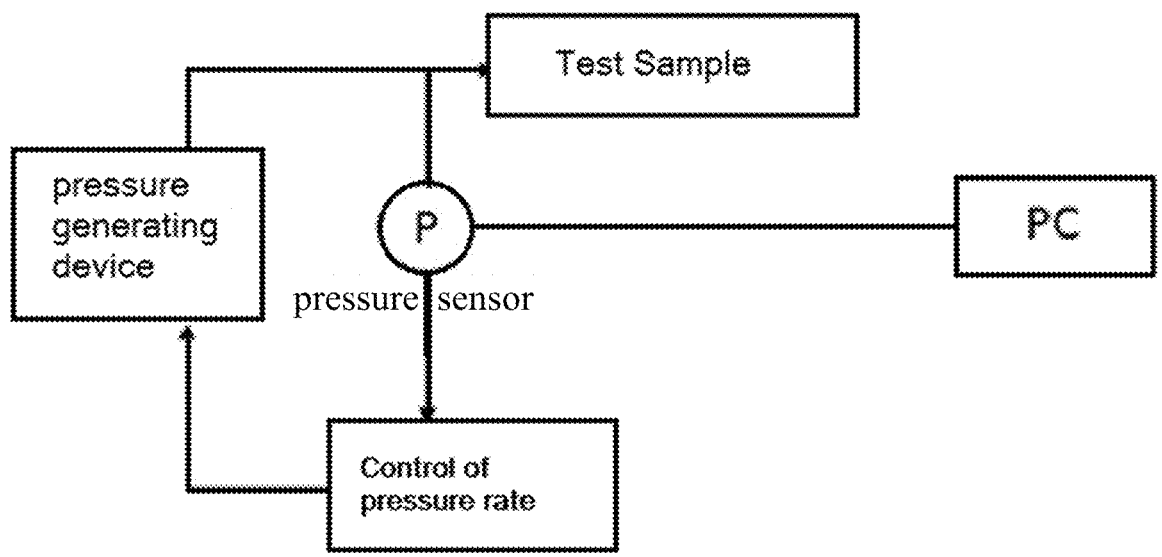
FIG. 10 shows an experimental setting of a hydraulic burst pressure test, wherein in A, a schematic overview is shown, and in B, the fixation of the TEVG in the experimental setting is shown.
Figure 10B:
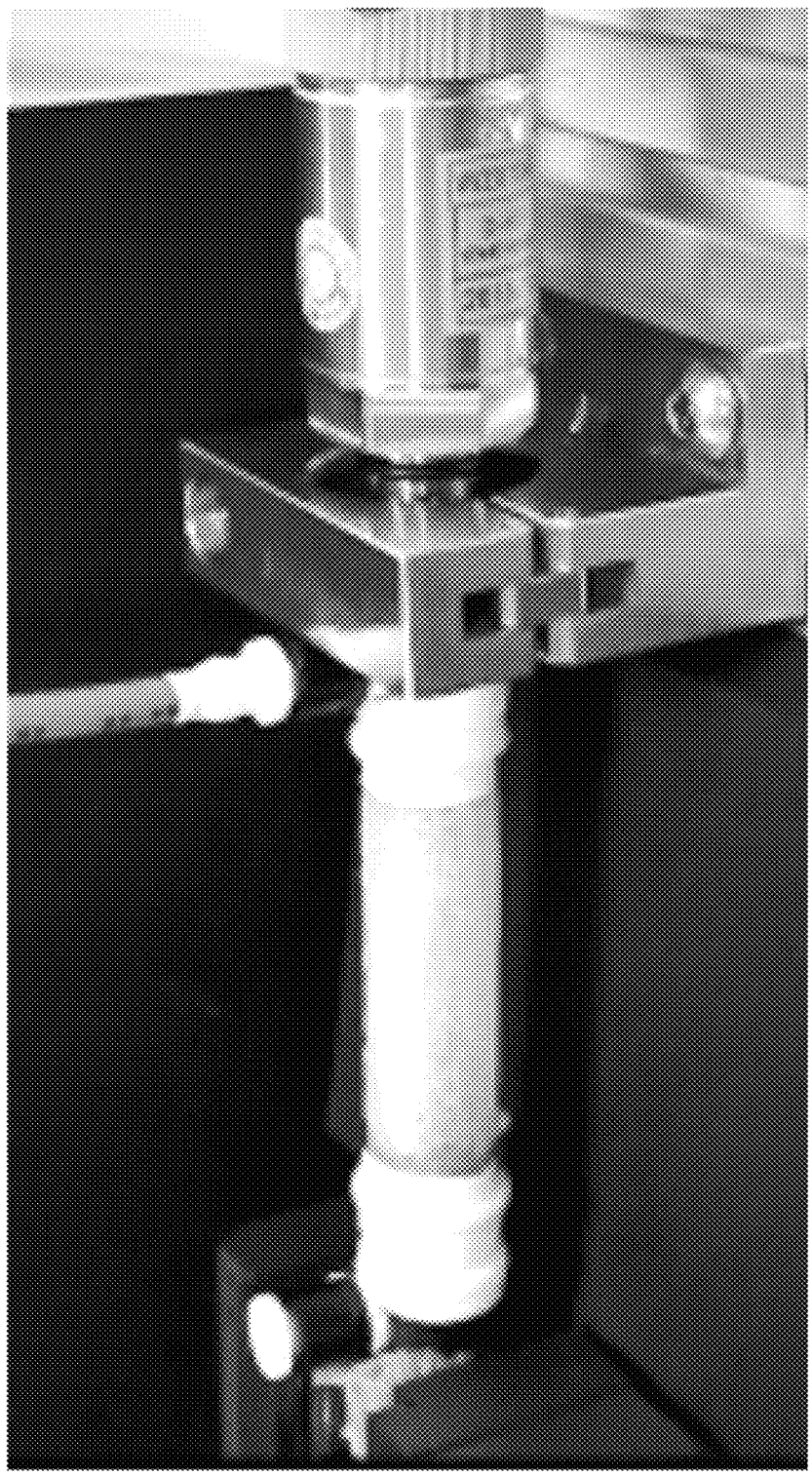
Figure 11:
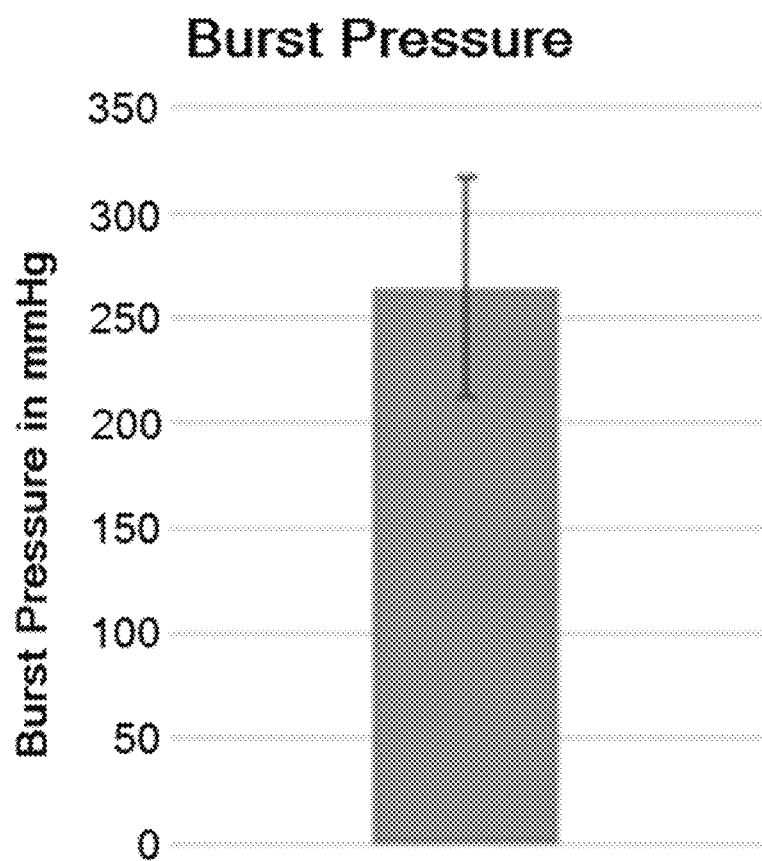
FIG. 11 shows the results of the burst pressure testing (n=4) according to FIG. 10.

Hemodynamics by blood flow and blood pressure induce biomechanical forces on vessel walls. To assess the mechanical resilience of the TEVG, burst tests have been performed to evaluate the conditions under which rupture of the TEVG is induced. For this purpose, a complete TEVG of Example 1 was rehydrated for 20 min in 0.9% NaCl solution. After rehydration the vascular graft was applied to the test setup and exposed to increasing hydraulic pressures using distilled water as fluid element. During testing the pressure rise was recorded. The pressure was increased until the TEVG ruptured (see FIG. 10). At increasing hydraulic pressures, formation of small holes were observed. At hydraulic pressures of 264±52 mmHg rupture of the TEVG was observed (see FIG. 11).

To determine the residual water content in the TEVG, a Karl Fischer titration according to Ph. Eur. 2.5.12 is performed. The residual water content in 7 TEVG derived from 5 different production batches was determined an in average 4.1+/−0.5% (w/w) (not depicted).

Figure 12:
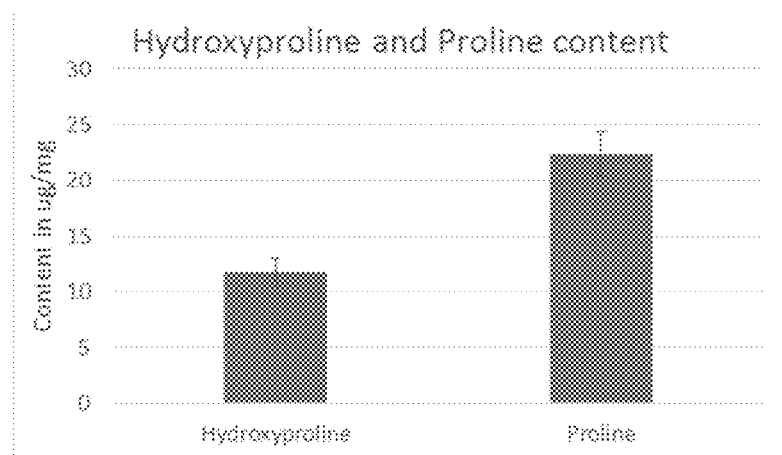
FIG. 12 shows the hydroxyproline and proline content measured in sample TEVGs (n=5)

The HYP-content in 5 TEVG (of three different production batches) was analyzed according to Ph. Eur. 2.2.56. and was in average 11.7+/−0.8 μg/mg (w/w; average+/−stdev) (see FIG. 12).

Figure 13:
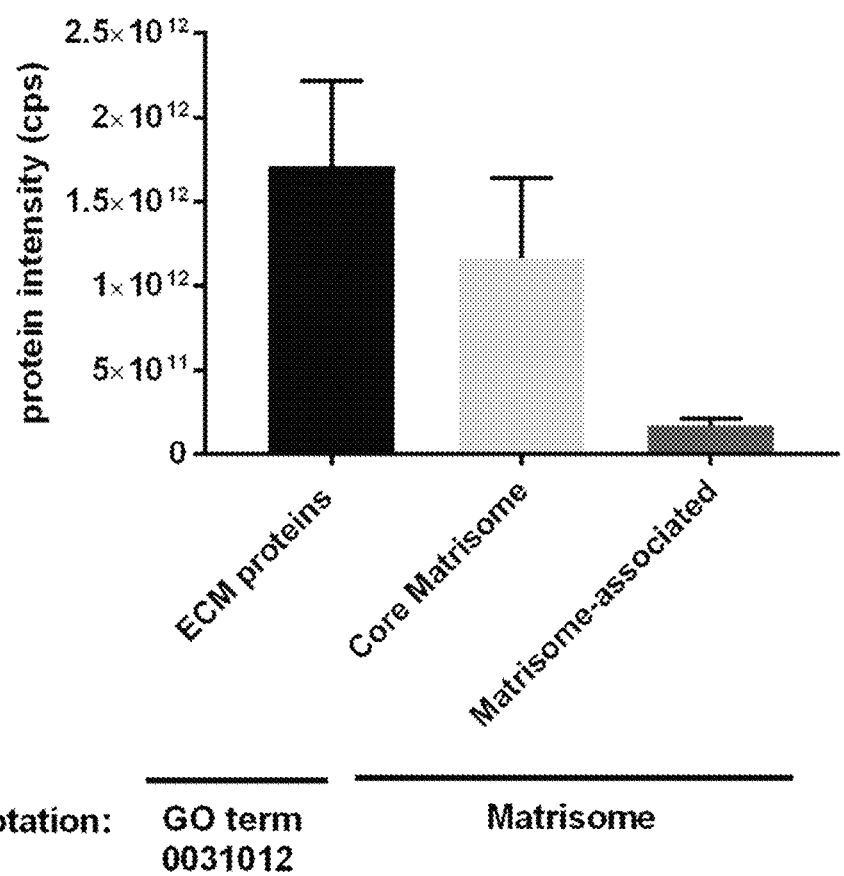
FIG. 13 shows the results of shotgun MS analysis of sample TEVGs (n=12), followed by annotation of the detected peptides using gene ontology (GO) term 0031012 that allows to assign the peptides to the class of ECM-proteins, as well as Matrisome-annotation. Protein intensities (cps) of ECM-proteins are shown, as well as protein intensities of core-Matrisome and Matrisome-associated proteins.
Figure 14:
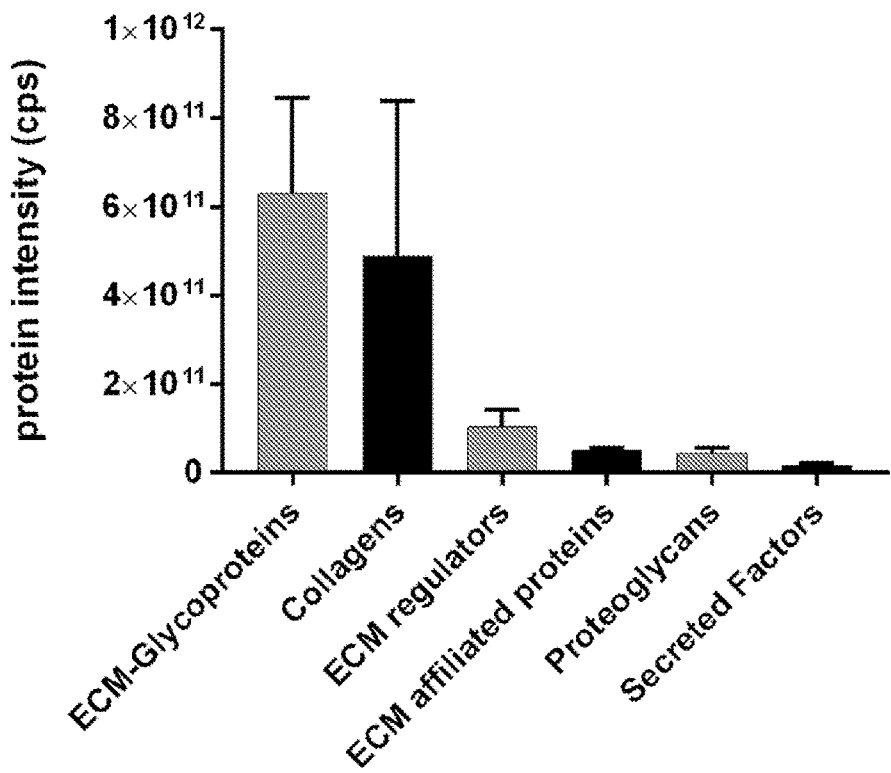
FIG. 14 shows the results of shotgun MS analysis of sample TEVGs followed by annotation using "Matrisome Project" categories, wherein protein intensities (cps) of the proteins that were assigned to the indicated classes, are shown.

In order to determine the proteineous composition of the decellulized TEVG, mass spectrometry (MS) analysis was performed. For this purpose, TEVG-samples were first digested (on-matrix protocol: protein reduction, alkylation and trypsin digestion) and subsequently acquired in shotgun LC-MS/MS mode. LC-MS/MS data were searched using a human UniProt database, and ECM proteins were annotated based on GO term 0031012 and with the "Matrisome Project" functional protein categories, in order to characterize the composition of the ECM present in TEVG in more detail (see FIG. 13). The Matrisome Project allows prediction of the ensemble of extracellular matrix and ECM-associated proteins (http://web.mit.edu/hyneslab/matrisome/). Protein annotation based on the "Matrisome Project" categories turned out to be more selective compared to GO term 0031012. The "Matrisome project" annotation also allows a classification of proteins in the following categories: ECM-glycoproteins; collagens; ECM-regulators; ECM-affiliated proteins; proteoglycans; secreted factors (see FIG. 14).

The steps of assessment of further mechanical properties described above for the TEVG according to Example 1 is also applicable to the production of other types of TEMDs.

Figure 15A:
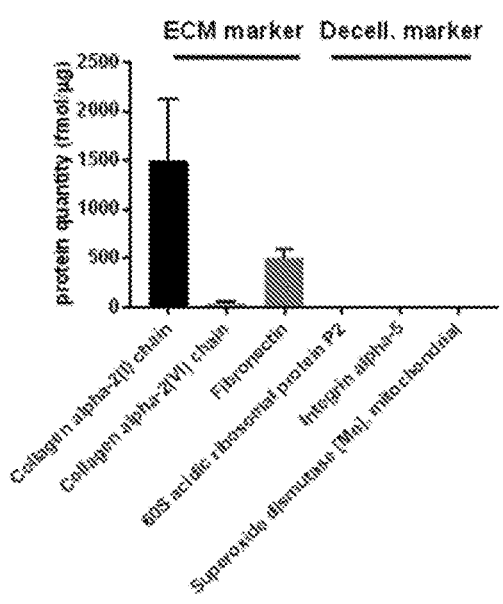
FIG. 15 shows the results of an MS analysis of ECM markers and decellularization markers in sample TEVGs, wherein in A, an absolute quantification of the indicated markers by using reference peptides of known concentration is shown, and in B, a relative quantification of the indicated markers is shown.
Figure 15B:
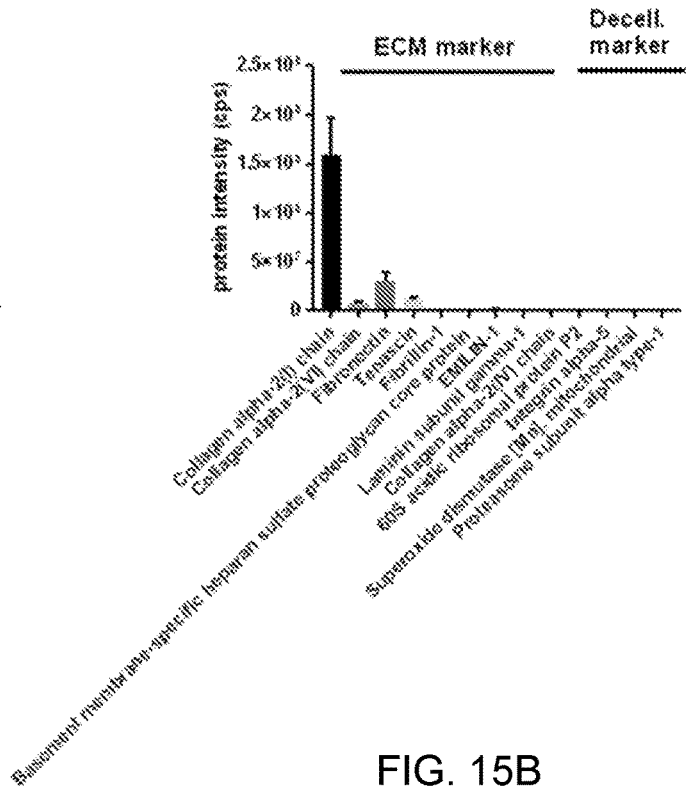

In order to quantify markers for extracellular matrix present in TEVG in an absolute manner, reference peptides for three ECM marker proteins were used (collagen alpha-2(I) chain; collagen alpha-2(VI) chain and fibronectin). Furthermore, to demonstrate that the decellularization process during production of the TEVG worked effectively, reference peptides for three decellularization markers (60S acidic ribosomal protein P2; integrin alpha-5, and superoxide dismutase [Mn] mitochondrial)" were used. Absolute quantification of these ECM- and decellularization markers is depicted in FIG. 15A. Additional ECM- and decellularization markers were analysed, however this quantification is only relative since no reference peptides were applied for their quantification (see FIG. 15B). Altogether, the analysis of these ECM- and decellularization markers confirmed that the decellularization step performed during the production of the TEVG removes unwanted cellular components while it preserves the ECM.

The TEMD according to the present invention is composed of human proteins (mainly ECM-proteins) and the biodegradable polymers poly-4-hydroxybutyrate (P4HB) and polyglycolic acid (PGA). The production of the inventive TEMD starts with the production of polymer scaffolds (composed of PGA and P4HB) that are subsequently seeded with cells. With seeding of cells on the polymer scaffold degradation of the polymers by hydrolysis is initiated, especially for the fast degrading PGA. In order to monitor the contents of the polymers in the final TEMD product, the polymers of the TEVG of Example 1 were extracted of the final product using an eluent and subsequently analyzed by size exclusion chromatography (SEC) at the contract company PSS Polymer Services GmbH, Mainz, Germany. Size exclusion chromatography characterized the molecular weight distribution of the extracts and by calibrating with pure samples of the polymer starting materials (PGA, P4HB; see FIG. 16A) of known concentration, the content of each polymer was evaluated in a semi-quantitative manner. Using this approach, a P4HB content of 40.7+/−4.6% (w/w) and a PGA content of 17.1+/−4.1% (w/w) was determined in the tested TEVG-samples (n=7 of five production batches; average+/−stdev) (see FIG. 16B).

Figure 16A:
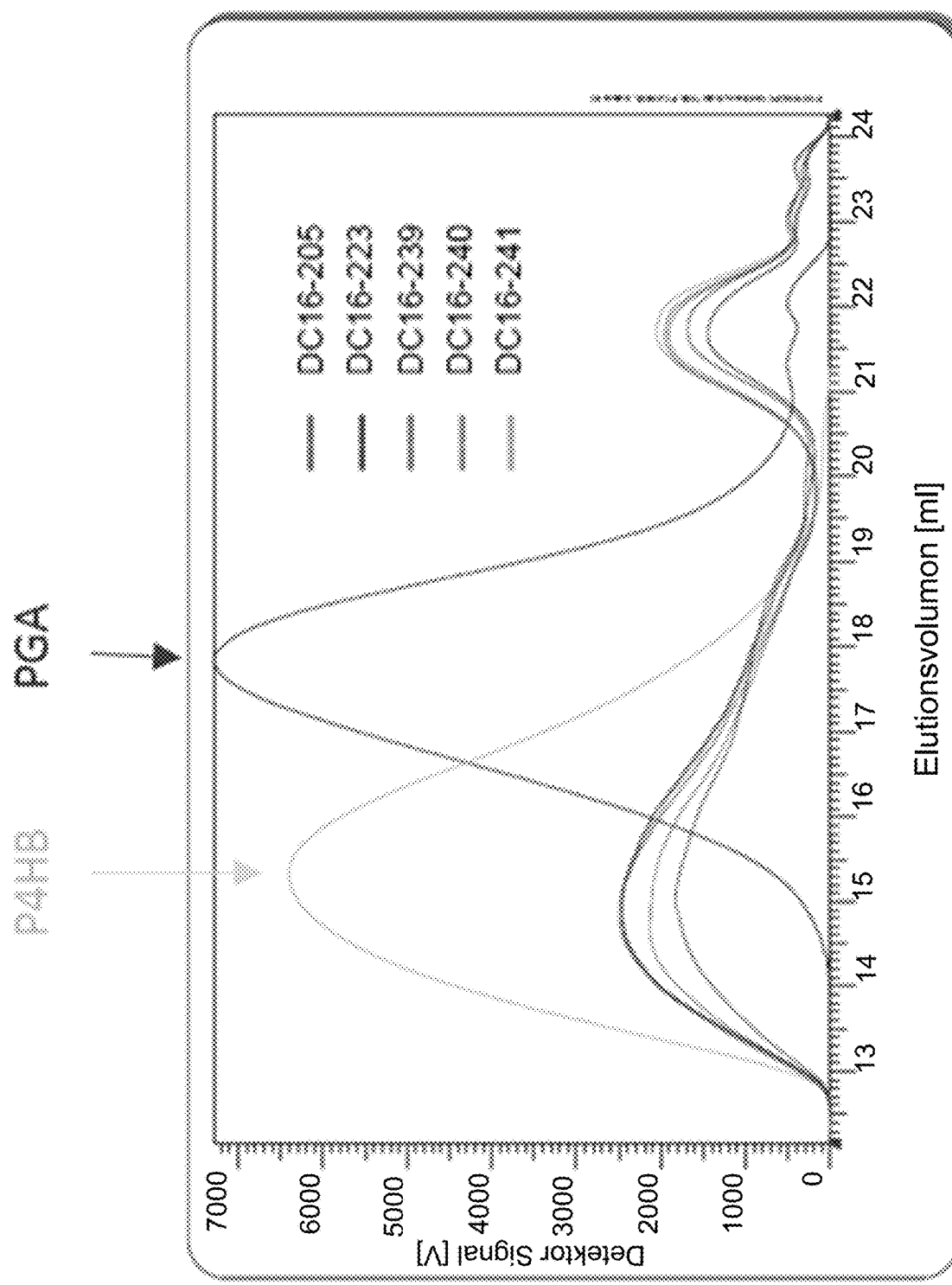
FIG. 16 shows, in A, a size exclusion chromatography (SEC) of a sample TEVG to determine the PGA and P4HB content, and in B, the content of P4HB and PGA measured in the sample TEVG.
Figure 16B:
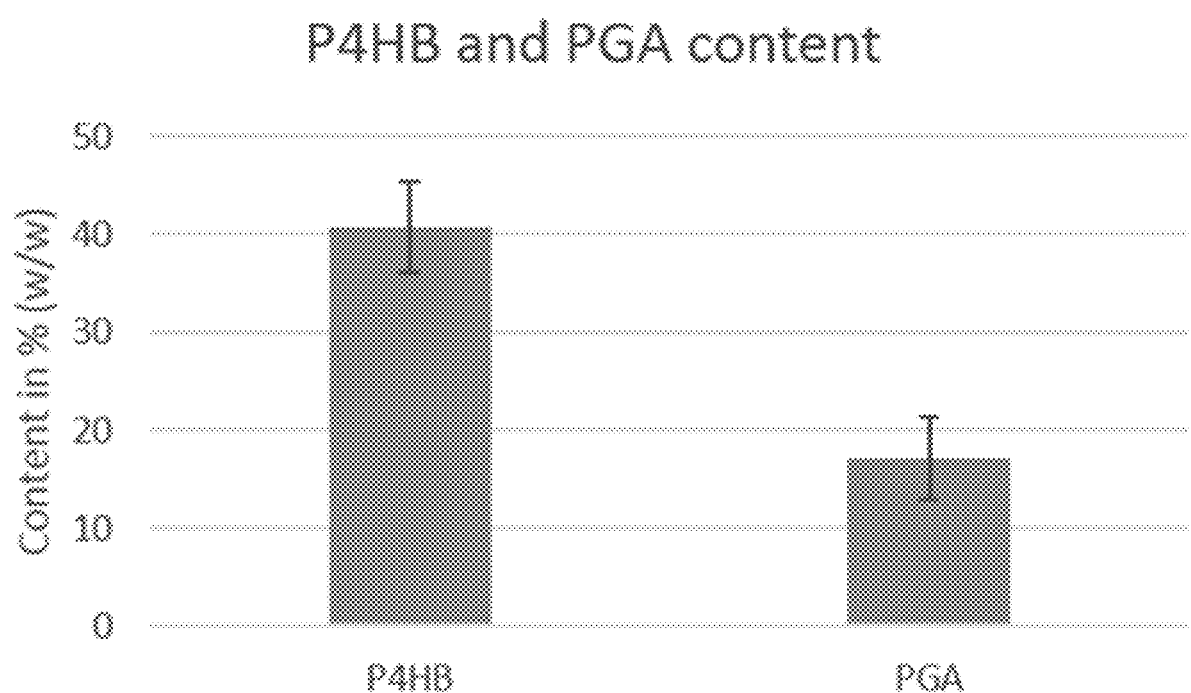

In the size exclusion chromatography (SEC) of a sample vascular graft to determine the PGA and P4HB content according to FIG. 16A, the content of PGA and P4HB was evaluated by spiking with pure polymer solutions (PGA or P4HB, indicated with arrows) of known concentrations.

Figure 17A:
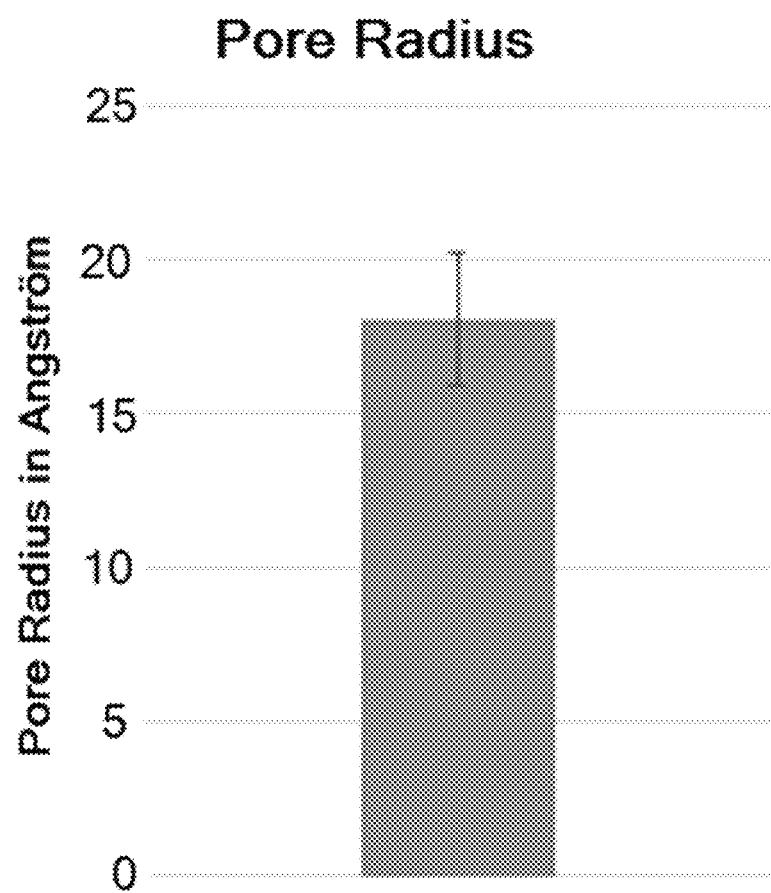
FIG. 17 shows, in A, the pore radius, in B, the pore volume, and in C, the specific surface area measured in sample TEVGs (n=8)
Figure 17B:
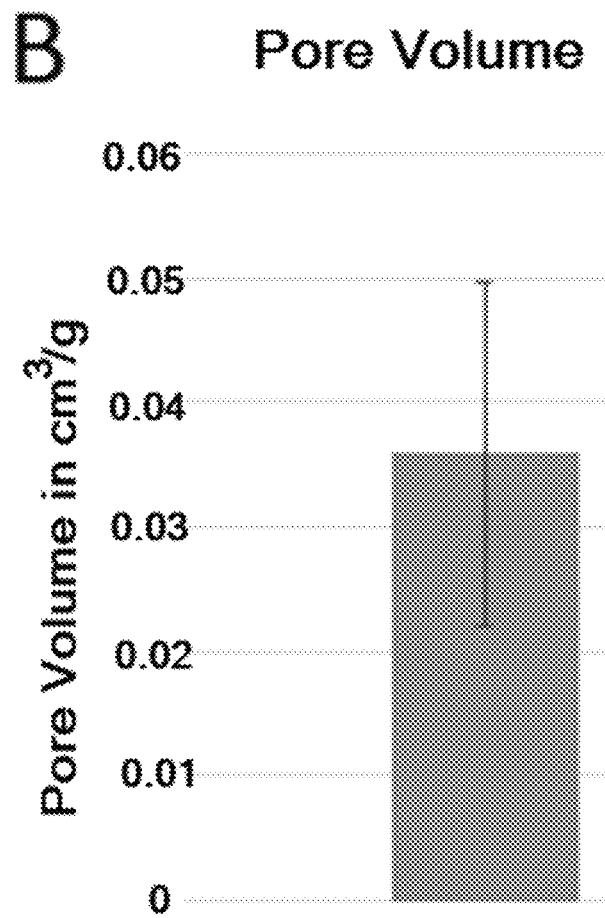
Figure 17C:
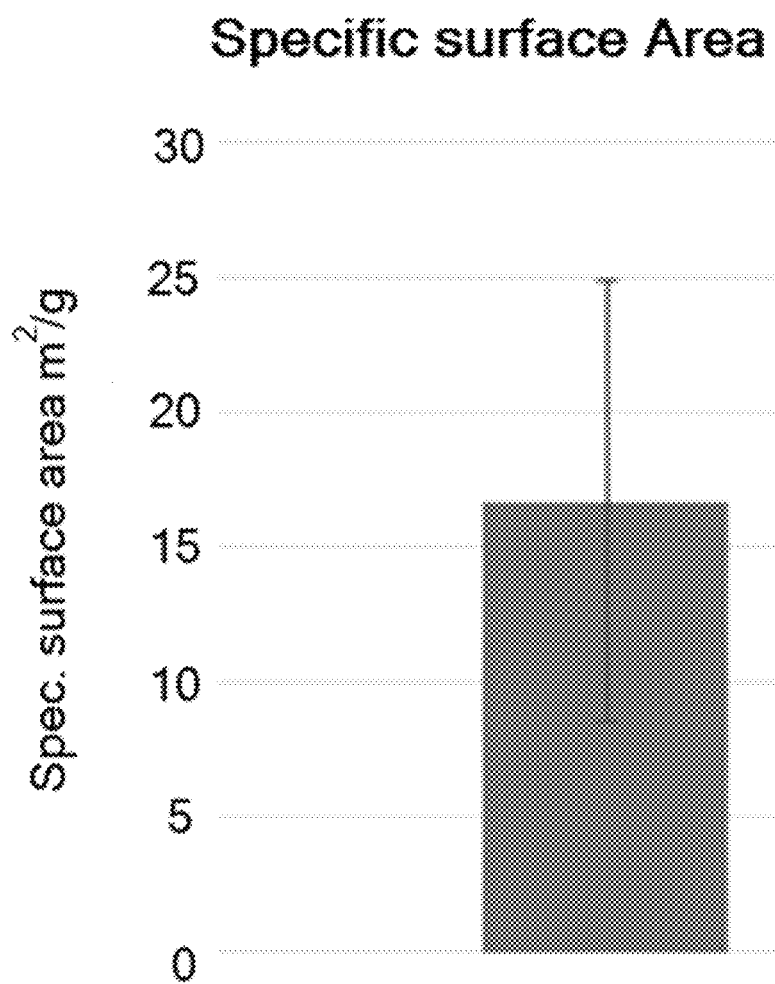

Gas adsorption analysis is commonly used for surface area and porosity measurements. This involves exposing solid materials to gases (Nitrogen gas is generally employed) at a variety of conditions and evaluating either the weight uptake or the sample volume. Analysis of these data provides information regarding the physical characteristics of the solid including: porosity, total pore volume and pore size. Porosity of the TEVG was determined by the method of Barrett, Joyner, and Halenda (BJH) which applies to the mesopore and small macropore size range. Results are depicted in FIG. 17.

Figure 18:
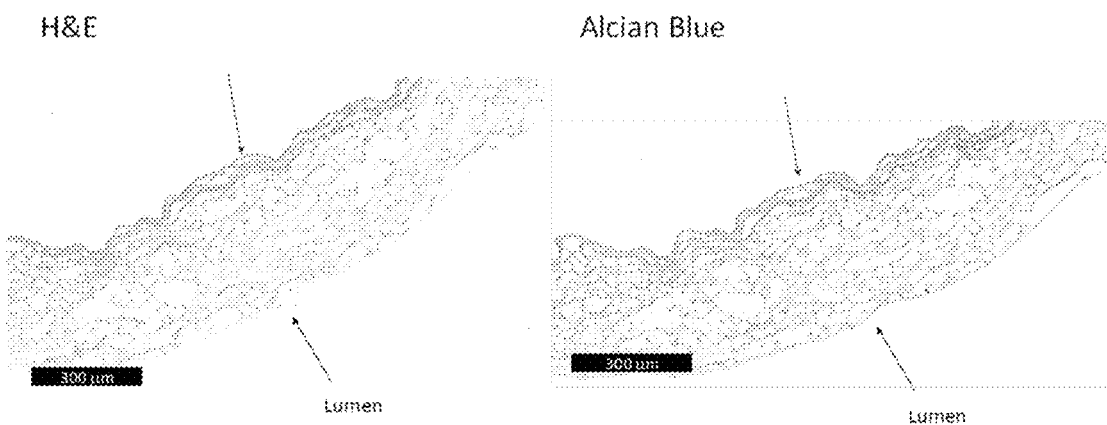
FIG. 18 shows hematoxylin/eosin (H&E) staining and Alcian blue staining of a sample TEVG (n=1)

To analyze the structural composition of the TEVG and visualize particular components, standard histology analysis was performed at the Institut Mutualiste Montsouris (IMM), Paris, France. A hematoxylin/eosin (H&E) staining was used to visualize tissue structure and to confirm the absence of nuclei/DNA and an Alcian Blue staining was used to visualize glycosaminoglycans. Glycosaminoglycans are abundant in ECM and hence a marker for ECM. The representative H&E and Alcian blue stainings of the TEVG shown in FIG. 18 confirm the absence of nuclei and the presence of ECM, respectively. In both stainings the porous nature of the TEVG is discernible. The outside of the TEVG, that notably is composed of several layers of P4HB that are sprayed during the production of the polymer scaffold, are marked with the red arrow in FIG. 18.

Figure 19:
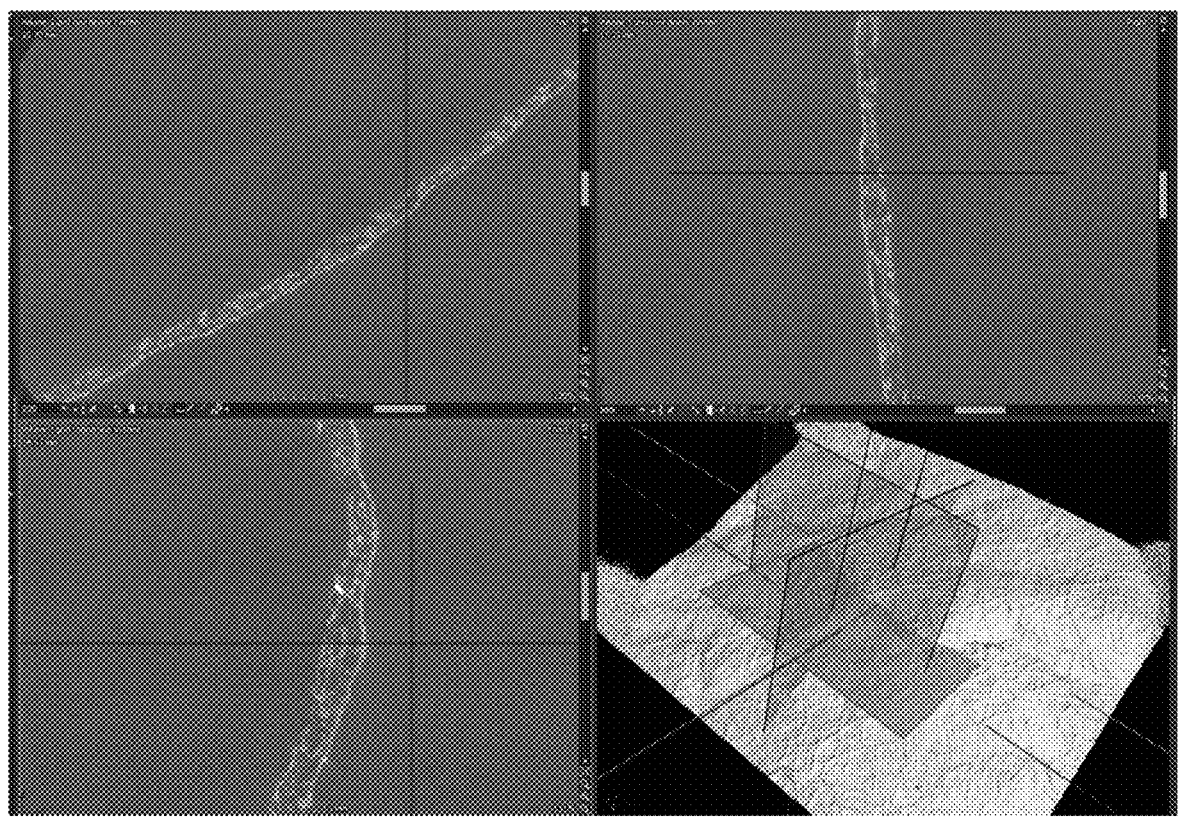
FIG. 19 shows a microCT analysis of a sample TEVG (n=1)

To analyse the wall thickness and structure of TEVG, X-ray microtomography (microCT) was performed (see FIG. 19). microCT uses x-rays to create cross-sections of a physical object that can be used to recreate a virtual model (3D model) without destroying the original object. The prefix micro-($\mu$) is used to indicate that the pixel sizes of the cross-sections are in the micrometre range.

The quality control steps described above are applicable to the production of other types of TEMDs.

Implantation of the TEVG:

Implantation of the TEVG of Example 1 is to be performed by anastomosis to the IVC (vena cava inferior) and pulmonary artery by suture ligation. To assess the mechanical stability and, thus safety of the suture, suture retention tests have been performed. For this purpose, a suture (string made of stainless steel with the diameter of 0.14 mm, which corresponds to prolene 5/0 suture) was inserted 2 mm from the end of a rehydrated TEVG sample through one wall of the device to form a half loop (see FIG. 8A). The suture was pulled at a rate of 100 mm/min and the force required to pull the suture through the device was recorded (Equipment used: Load cell, Instron, 2530-437; Universal testing machine, Instron, 5944). Suture retention strength of 7 TEVG was measured and in average a force of 0.82+/−0.25 N (corresponding to 82 g) had to be applied to pull the suture through the device (see FIG. 8B). The assessment of mechanical stability mentioned above is also applicable to the production of other types of TEMDs.

Example 2: Production of a Tissue-Engineered Sinus Valve

Figure 20:
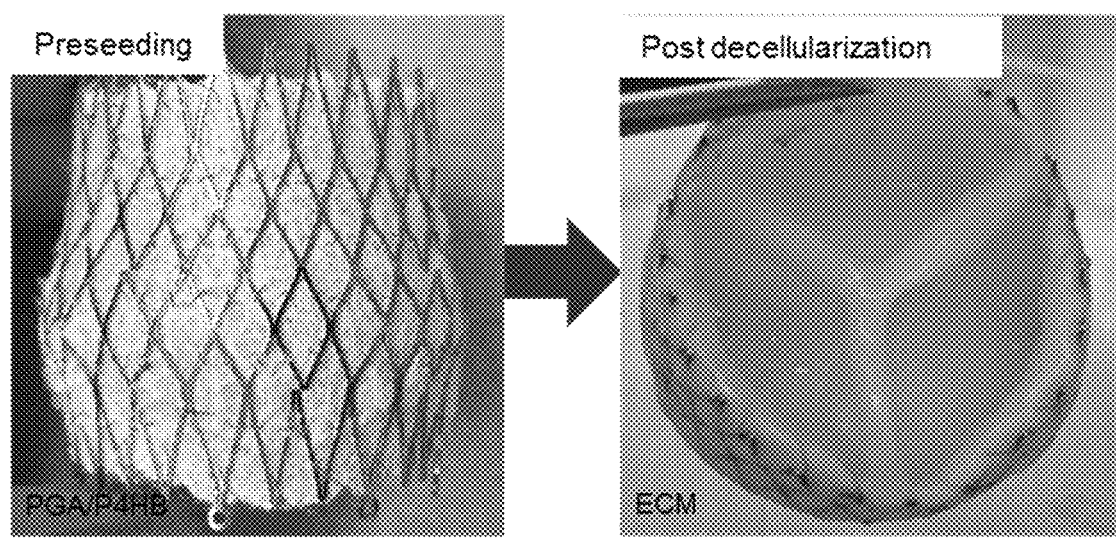
FIG. 20 shows, according to a second exemplary embodiment of the invention, a PGA-mesh sutured into a nitinol sinus-stent prior to seeding and the resulting tissue engineered tri-leaflet heart valve after decellularization.

According to a second exemplary embodiment of the present invention, a tri-leaflet heart valve scaffold was made from a non-woven PGA mesh and finally integrated into a nitinol sinus-stent by using continuous sutures (as shown in FIG. 20). The PGA-scaffold was coated with 1% P4HB, overnight dried, and sterilized with EtOH, Pen-Strep (Penicillin-Streptomycin; 10,000 U/ml), and amphothericine. Finally, the PGA-scaffold was incubated overnight at 37° C. with an optimized growth medium comprising advanced DMEM supplemented with 1% Pen-Strep Solution, 1% Glutamax, 10% FBS and 130 mg Vit. C (per 500 ml).

Thereafter, the valve was seeded with human dermal fibroblasts ($1\times10^6$ cells/cm$^2$) using fibrin as a cell carrier. After seeding, the scaffold was placed, preferably in a closed configuration of the leaflets, into a dual pulse duplicator system for 4 weeks of culture. During valve culture, inserts were used to impose a physiological valve geometry. Vit. C or TGF-$\beta$ were used as optional supplements in the medium to enhance ECM production. The decellularization process was performed as described for Example 1.

The sinus valve, being designed for the replacement of a respective sinus valve in the pulmonary artery, serves as an example for the production of heart valve replacement grafts.

Example 3: Production of a Tissue-Engineered Patch

Figure 21:
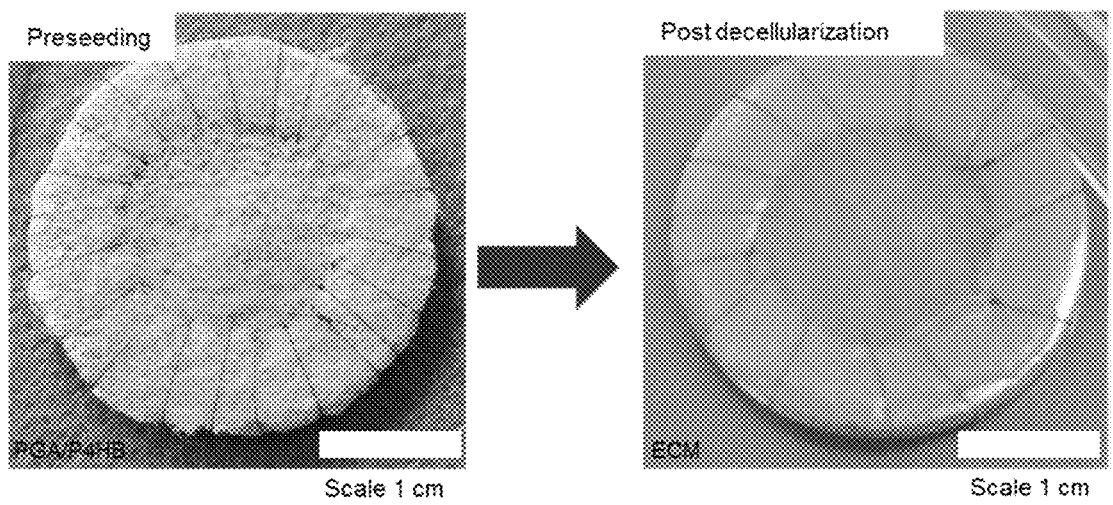
FIG. 21 shows, according to a third exemplary embodiment of the invention, a PGA-mesh sutured onto a metal stainless steel ring prior to seeding and the resulting tissue engineered patch after decellularization.

According to a second exemplary embodiment of the present invention, a PGA-scaffold was cut (circular or strip) and coated with 1% P4HB. After overnight drying, the patch was sutured onto a metal stainless steel ring (as shown in FIG. 21) and sterilized with EtOH, Pen-Strep, and amphothericine. Next, the patch was incubated overnight at 37° C. with an optimized growth medium comprising advanced DMEM supplemented with 1% Pen-Strep Solution, 1% Glutamax, 10% FBS and 130 mg Vit. C (per 500 ml). Thereafter, human dermal fibroblasts were seeded onto the patch using fibrin as a cell carrier. After seeding, the patch was placed in small medium jar and cultured for 4 weeks by using an orbital shaker to enhance medium distribution. Also for the production of the patch, Vit. C or TGF-$\beta$ were used as optional supplements in the medium to enhance ECM production. The decellularization process was performed as described for Example 1.

REFERENCES

1. Langer, R. & Vacanti, J. P. Tissue Engineering. Science 260, 920-926, doi:DOI 10.1126/science.8493529 (1993).
2. Asti, A. & Gioglio, L. Natural and synthetic biodegradable polymers: different scaffolds for cell expansion and tissue formation. Int J Artif Organs 37, 187-205, doi:10.530/ijao.5000307 (2014).
3. Dunn, A. S., Campbell, P. G. & Marra, K. G. The influence of polymer blend composition on the degradation of polymer/hydroxyapatite biomaterials. J Mater Sci Mater Med 12, 673-677 (2001).
4. Sugiura, T. et al. Tropoelastin inhibits intimal hyperplasia of mouse bioresorbable arterial vascular grafts. Acta Biomater 52, 74-80, doi:10.1016/j.actbio.2016.12.044 (2017).
5. Mol, A. et al. Autologous human tissue-engineered heart valves: prospects for systemic application. Circulation 114, 1152-158, doi:10.1161/CIRCULATIONAHA.105.001123 (2006).
6. Weber, B. et al. Injectable living marrow stromal cell-based autologous tissue engineered heart valves: first experiences with a one-step intervention in primates. Eur Heart J 32, 2830-2840, doi:10.1093/eurheartj/ehr059 (2011).
7. Li, H., Du, R. & Chang, J. Fabrication, characterization, and in vitro degradation of composite scaffolds based on PHBV and bioactive glass. J Biomater Appl 20, 137-155, doi:10.1177/0885328205049472 (2005).
8. Chen, G. Q. & Wu, Q. The application of polyhydroxyalkanoates as tissue engineering materials. Biomaterials 26, 6565-6578, doi:10.1016/j.biomaterials.2005.04.036 (2005).
9. Shinoka, T. et al. Creation of viable pulmonary artery autografts through tissue engineering. J Thorac Cardiov Sur 115, 536-545, doi:Doi 10.1016/S0022-5223(98) 70315-0 (1998).
10. Schmidt, D., Stock, U. A. & Hoerstrup, S. P. Tissue engineering of heart valves using decellularized xenogeneic or polymeric starter matrices. Philos Trans R Soc Lond B Biol Sci 362, 1505-1512, doi:10.1098/rstb.2007.2131 (2007).
11. Hoerstrup, S. P. et al. Functional living trileaflet heart valves grown in vitro. Circulation 102, III44-49 (2000).
12. Weber, B. et al. Off-the-shelf human decellularized tissue-engineered heart valves in a non-human primate model. Biomaterials 34, 7269-7280, doi:10.1016/j.biomaterials.2013.04.059 (2013).
13. Hoerstrup, S. P. et al. Living, autologous pulmonary artery conduits tissue engineered from human umbilical cord cells. Ann Thorac Surg 74, 46-52; discussion 52 (2002).
14. Hoerstrup, S. P. et al. Early failure of the tissue engineered porcine heart valve SYNERGRAFT in pediatric patients. Eur. J. Cardiothorac. Surg. 2003; 23:1002-6.
15. Agrawal C. M. et al., Biodegradable polymeric scaffolds for musculoskeletal tissue engineering. J. Biomedic. Mat. Res. 2001; 55:141-50.
16. Niklason et al., Functional arteries grown in vitro, Science, 1999; 284: 489-93.
17. D. Schmid, S. P. Hoerstrup, "Tissue engineered heart valves based on human cells", Swiss Med. Wkly. 2005; 135: 618-623.

The invention claimed is:

1. A method for production of a tissue-engineered medical device, comprising the following steps:
A.) providing a polymer scaffold, said polymer scaffold comprising a substrate comprising polyglycolic acid, and a coating comprising poly-4-hydroxybutyrate ('P4HB');
B.) application of a cell suspension containing isolated and expanded cells to the polymer scaffold, thereby producing a seeded polymer scaffold;
C.) placement of the seeded polymer scaffold in a bioreactor and mechanical stimulation by exposure to a pulsatile flux of incremental intensity, thereby forming a tissue-engineered medical device comprising an extracellular matrix;
D.) mounting of the tissue-engineered medical device on a conduit stabilizer and incubation under static conditions in a cell culture medium;
E.) decellularisation of the tissue-engineered medical device in a washing solution comprising a detergent;
F.) nuclease treatment of the tissue-engineered medical device;
G.) rinsing of the tissue-engineered medical device.

2. The method for the production of a tissue-engineered medical device according to claim 1, characterized in that step A.) comprises the following steps:
providing a mesh comprising polyglycolic acid ('PGA') as the substrate for the polymer scaffold;
in a first coating step, coating the mesh with a solution containing poly-4-hydroxybutyrate;
sterilizing the polymer scaffold;
and incubating the polymer scaffold in a cell culture medium.

3. The method for the production of a tissue-engineered medical device according to claim 2, wherein the tissue-engineered medical device is a vascular graft, and wherein after the first coating step and prior to sterilization, the method comprises the following steps:
shaping the coated mesh to a tube, thereby forming a tubular polymer scaffold;
in a second coating step, coating the tubular polymer scaffold, with a solution containing poly-4-hydroxybutyrate ('P4HB').

4. The method for the production of a tissue-engineered medical device according to claim 3, wherein in step B.) the cell suspension containing isolated and expanded cells is applied only to an inner surface of the tubular polymer scaffold.

5. The method for the production of a tissue-engineered medical device according to claim 3, wherein after shaping the coated mesh to a tube, the method further comprises the step of fixing edges of the mesh by heating them to at least 60 degrees Celsius, thereby forming a tubular polymerscaffold.

6. The method for the production of a tissue-engineered medical device according to claim 3, wherein in the second coating step, the coating of the tubular polymer scaffold with a solution containing poly-4-hydroxybutyrate is carried out only on an outer side of the tube.

7. The method for the production of a tissue-engineered medical device according to claim 3, wherein the second coating step is carried out by spray coating.

8. The method for the production of a tissue-engineered medical device according to claim 1, wherein in step B.), the cells contained in the cell suspension are human cells selected from a group consisting of fibroblasts, mesenchymal stem cells, mononuclear cells, and endothelial progenitor cells.

9. The method for the production of a tissue-engineered medical device according to claim 8, wherein in step B.), the cells contained in the cell suspension are human cells derived from a source selected from a group consisting of bone marrow, blood, adipose tissue, amniotic fluid, chorionic villi, umbilical cord matrix, and umbilical cord blood.

10. The method for the production of a tissue-engineered medical device according to claim 8, wherein in step B.), the cells contained in the cell suspension are human fibroblasts derived from a human umbilical cord vein.

11. The method for the production of a tissue-engineered medical device according to claim 1, wherein in step B.) at least 0.5-5 million cells/cm$^2$ are seeded on the polymer scaffold.

12. The method for the production of a tissue-engineered medical device according to claim 11, wherein in step B.) 2-4 million cells/cm$^2$ are seeded on the polymer scaffold.

13. The method for the production of a tissue-engineered medical device according to claim 1, wherein the cell suspension applied in step B.) is prepared by a method comprising the following steps:
isolation of the cells, selected from a group consisting of fibroblasts, mesenchymal stem cells, mononuclear cells, and endothelial progenitor cells; subsequently expansion of the cells, subsequently harvesting of the isolated and expanded cells;

subsequently forming a cell suspension by adding a cell carrier solution comprising a gelling agent to the isolated and expanded cells.

14. The method for the production of a tissue-engineered medical device according to claim 13, wherein the cell suspension applied in step B.) is prepared by a method comprising all of the following steps:
   isolation of cells, wherein the cells are human cells selected from a group consisting of fibroblasts, mesenchymal stem cells, mononuclear cells, and endothelial progenitor cells, derived from a source selected from a group consisting of: bone marrow, blood, adipose tissue, amniotic fluid, chorionic villi, umbilical cord matrix, umbilical cord blood;
   expansion of the isolated cells in at least one culture vessel for 5-8 days;
   harvesting of the isolated cells;
   forming a cell suspension by adding a cell carrier solution comprising a gelling agent to the isolated cells.

15. The method for the production of a tissue-engineered medical device according to claim 13, wherein the cell suspension is formed by adding a cell carrier solution comprising fibrinogen and purified thrombin, to the isolated and expanded cells, wherein the cell suspension is formed by first adding purified fibrinogen to the isolated and expanded cells to form a first cell suspension, and subsequently adding purified thrombin to the first cell suspension to form a second cell suspension which then serves as the cell suspension for application to the polymer scaffold in step B.).

16. The method for the production of a tissue-engineered medical device according to claim 1, wherein the method further comprises at least one of the following steps after the step of rinsing of the tissue-engineered medical device:
   lyophilisation of the tissue-engineered medical device;
   packaging of the tissue-engineered medical device;
   sterilization of the tissue-engineered medical device.

17. The method for the production of a tissue-engineered medical device according to claim 16, wherein the method further comprises all of the following steps:
   lyophilisation of the tissue-engineered medical device;
   packaging of the tissue-engineered medical device;
   sterilization of the tissue-engineered medical device by ethylene oxide treatment.

18. The method for the production of a tissue-engineered medical device according to claim 1, wherein the method further comprises one or more of the following steps of in-process quality control:
   determination of a content of P4HB in the polymer scaffold, wherein thean acceptance criterion for the content of P4HB in the polymer scaffold is that the content of P4HB in the polymer scaffold is in the range of 5-95% w/w;
   ensuring of homologous deposition of P4HB on a mesh of the polymer scaffold;
   examination of cells to be seeded on the polymer scaffold prior to seeding in terms of cell identity, proliferation, viability and lack of pathogens;
   control of a coagulation time of the cell suspension;
   control of a number of cells seeded on the polymer scaffold;
   control of homogenous application of cells to the polymer scaffold;
   control of medium composition in the bioreactor;
   control of lactate value at each medium change in the bioreactor;
   control of formation of the extracellular matrix in the bioreactor.

19. The method for the production of a tissue-engineered medical device according to claim 18, wherein during a quality control of cells to be seeded on the polymer scaffold prior to seeding, a cell identity is determined via flow cytometry, and/or wherein a proliferation capacity is determined by measuring a doubling time, wherein a preferred acceptance criterion for the doubling time is less than 100 hours.

20. The method for the production of a tissue-engineered medical device according to claim 18, wherein the method further comprises all of the following steps of in-process quality control:
   determination of a content of P4HB in the polymer scaffold, wherein the acceptance criterion for the content of P4HB in the polymer scaffold is that the content of P4HB in the polymer scaffold is in the range of 5-95% w/w;
   ensuring of homologous deposition of P4HB on the mesh of the polymer scaffold;
   examination of cells to be seeded on the polymer scaffold prior to seeding in terms of cell identity, proliferation, viability and lack of pathogens;
   control of the coagulation time of the cell suspension;
   control of number of the cells seeded on the polymer scaffold;
   control of homogenous application of the cells to the polymer scaffold;
   control of medium composition in the bioreactor;
   control of lactate value at each medium change in the bioreactor;
   control of formation of extracellular matrix in the bioreactor by mass spectrometry by using human procollagen type I C-terminal propeptide as a suitable marker.

21. The method for the production of a tissue-engineered medical device according to claim 1, wherein the method further comprises at least one of the following steps of quality control of a finished tissue-engineered medical device:
   verification of sterility;
   measurement of endotoxin content;
   measurement of mycoplasma content;
   measurement of residual DNA content;
   measurement of residual water content;
   measurement of polymer content;
   measurement of hydroxyprolin content;
   measurement of protein content, by determining a content of extracellular matrix proteins;
   measurement of thickness;
   suture retention test;
   tensile strength test;
   burst pressure test.

22. The method for the production of a tissue-engineered medical device according to claim 21, wherein the method further comprises all of the following steps of quality control of a finished tissue-engineered medical device:
   verification of sterility;
   measurement of endotoxin content;
   measurement of mycoplasma content;
   measurement of residual DNA content;
   measurement of residual water content;
   measurement of polymer content;
   measurement of hydroxyprolin content;
   measurement of protein content by determining a content of at least one of the following proteins selected from the group consisting of: fibronectin, collagen alpha-2(I)

chain, collagen alpha-2(VI) chain; and/or by determining a content of at least one of the following proteins selected from the group consisting of: superoxide dismutase, 60S acidic ribosomal protein P2, integrin alpha 5;

measurement of thickness, by microscopic analysis, in a dry and/or rehydrated form, wherein an acceptance criterion for the thickness of the decellularized tissue-engineered medical device is a range of 0.1-0.6 mm in a dry form and/or 0.15-0.7 mm in a rehydrated form;

suture retention test, wherein an acceptance criterion is that the tissue-engineered medical device withstands more than 0.5 N;

tensile strength test, wherein an acceptance criterion is that the tissue-engineered medical device withstands more than 0.5 MPa;

burst pressure test, wherein an acceptance criterion is that the tissue-engineered medical device withstands a pressure more than 150 mmHg.

23. The tissue-engineered medical device produced by the method according to claim 1.

24. The tissue-engineered medical device according to claim 23, wherein the tissue-engineered medical device is selected from the group consisting of a vascular graft, a valvular graft and a tissue patch.

25. The tissue-engineered medical device according to claim 23, wherein the tissue-engineered medical device contains a polymer scaffold comprising a PGA-mesh which comprises a coating containing P4HB and an extracellular matrix developed on the polymer scaffold, and wherein the tissue-engineered medical device comprises one or more of the following features:

an endotoxin content of less than 0.29 EU/ml;
a mycoplasma content below a limit of detection;
a residual DNA content of less than 50 ng dsDNA per mg dry weight;
a residual water content of less than 5%;
a PGA content of 0-30%, and a P4HB content of 30-75% (w/w);
a hydroxyprolin content of more than 5 µg/mg;
a content of fibronectin of at least 100 fmol/µg, and/or a content of collagen alpha-2(I) chain of at least 200 fmol/µg, and/or a content of collagen alpha-2(VI) chain of at least 5 fmol/µg; and/or a content of superoxide dismutase of less than 3 fmol/µg, and/or a content of 60S acidic ribosomal protein P2 of less than 3 fmol/µg, and/or a content of integrin alpha-5 of less than 3 fmol/µg
a thickness of 0.15-700 µm;
a suture retention of at least 0.5 N;
a tensile strength of at least 0.5 MPa;
a burst pressure of more than 150 mmHg.

26. The tissue-engineered medical device according to claim 23 configured for use as a cardiovascular replacement graft in human or animal patients.

27. The tissue-engineered medical device according to claim 23 configured for use as a heart valve or as a patch in a human or animal patient with a defect of a cardiovascular system.

28. The tissue-engineered medical device of claim 23 configured for use in a treatment of a cardiovascular disease of a human or animal body.

29. The tissue-engineered medical device according to claim 23 configured for use in a treatment of a defect of a cavopulmonary connection in a human or animal patient.

30. The tissue-engineered medical device according to claim 23 configured for use as a replacement for a cavopulmonary connection in human pediatric patients with hypoplastic left-heart syndrome.

31. The tissue-engineered medical device according to claim 23 configured for use as a heart valve or as a patch in a human pediatric patient with a defect of the cardiovascular system.

32. The tissue-engineered medical device of claim 23 configured for use in a treatment of a cardiovascular disease of a body of a human pediatric patient.

33. The tissue-engineered medical device according to claim 23 configured for use in a treatment of a defect of a cavopulmonary connection in a human pediatric patient.

34. A method for treating a human or animal patient, wherein the patient is suffering from a defect of a cardiovascular system, the method comprising the step of using the tissue-engineered medical device according to claim 23 as a heart valve or as a patch.

35. The method according to claim 34, wherein the patient is a human pediatric patient suffering from a defect of cavopulmonary connection.

36. The method according to claim 35, wherein the patient is a human pediatric patient suffering from hypoplastic left-heart syndrome.

37. The tissue-engineered medical device produced by the method according to claim 1, wherein the tissue-engineered medical device contains a polymer scaffold comprising a PGA-mesh which comprises a coating containing P4HB and an extracellular matrix developed on the polymer scaffold, and wherein the tissue-engineered medical device comprises all of the following features:

an endotoxin content of less than 0.29 EU/ml;
a mycoplasma content below a limit of detection;
a residual DNA content of less than 50 ng dsDNA per mg dry weight;
a residual water content of less than 5%;
a PGA content of 0-30%, and a P4HB content of 30-75% (w/w);
a hydroxyprolin content of more than 5 µg/mg;
a content of fibronectin of at least 100 fmol/µg, and/or a content of collagen alpha-2(I) chain of at least 200 fmol/µg, and/or a content of collagen alpha-2(VI) chain of at least 5 fmol/µg; and/or a content of superoxide dismutase of less than 3 fmol/µg, and/or a content of 60S acidic ribosomal protein P2 of less than 3 fmol/µg, and/or a content of integrin alpha-5 of less than 3 fmol/µg
a thickness of 0.15-700 µm;
a suture retention of at least 0.5 N;
a tensile strength of at least 0.5 MPa;
a burst pressure of more than 150 mmHg.

* * * * *